(12) United States Patent
Paraketsov et al.

(10) Patent No.: US 12,370,016 B2
(45) Date of Patent: Jul. 29, 2025

(54) AUTOMATIC SEGMENTATION QUALITY ASSESSMENT FOR SECONDARY TREATMENT PLANS

(71) Applicant: Align Technology, Inc., San Jose, CA (US)

(72) Inventors: Vasily Paraketsov, Moscow (RU);
Grigoriy Yazykov, Balashikha (RU);
Andrey Romanov, Moscow (RU)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 17/473,903

(22) Filed: Sep. 13, 2021

(65) Prior Publication Data
US 2022/0079714 A1   Mar. 17, 2022

Related U.S. Application Data

(60) Provisional application No. 63/077,181, filed on Sep. 11, 2020.

(51) Int. Cl.
| | |
|---|---|
| *A61C 7/00* | (2006.01) |
| *A61C 9/00* | (2006.01) |
| *G06T 7/00* | (2017.01) |
| *G06T 7/246* | (2017.01) |
| *G06T 7/73* | (2017.01) |
| *G06T 17/20* | (2006.01) |

(Continued)

(52) U.S. Cl.
CPC ............ *A61C 7/002* (2013.01); *A61C 9/0053* (2013.01); *G06T 7/0016* (2013.01); *G06T 7/251* (2017.01); *G06T 7/75* (2017.01); *G06T 17/20* (2013.01); *G06T 19/20* (2013.01); *G16H 30/40* (2018.01); *A61C 2007/004* (2013.01); *G06T 2207/30036* (2013.01); *G06T 2207/30241* (2013.01); *G06T 2219/2021* (2013.01)

(58) Field of Classification Search
CPC . A61C 7/002; A61C 9/0053; A61C 2007/004; G06T 7/136; G06T 7/11; G06T 7/13; G06T 7/0012; G06T 5/002; G06T 17/205; G06T 19/20; G06T 2207/30036; G06T 2210/41; G06T 2219/2004; G06T 7/0016; G06T 7/251; G06T 7/75; G06T 17/20; G06T 2207/30241; G06T 2219/2021; G06T 2200/08; G06T 2207/10028; G06T 7/55; G16H 30/40; G16H 20/40; G16H 50/50
See application file for complete search history.

(56) References Cited

U.S. PATENT DOCUMENTS

| | | |
|---|---|---|
| 5,975,893 A | 11/1999 | Chishti et al. |
| 6,227,850 B1 | 5/2001 | Chishti et al. |
| 6,227,851 B1 | 5/2001 | Chishti et al. |

(Continued)

*Primary Examiner* — Maurice L. McDowell, Jr.
(74) *Attorney, Agent, or Firm* — Shay Glenn LLP

(57) ABSTRACT

Provided herein are apparatuses (e.g., systems) and methods for assisting in generating and segmenting a 3D dental model of a subject's dentition. A 3D dental model may be generated from a dental scan. The apparatuses described herein can determine if the subject has previously undergone a dental or orthodontic treatment, and the 3D dental model can be compared to prior 3D dental models from the previous treatment(s). In some examples, the 3D dental model can be updated or supplemented with data from the prior 3D dental models.

23 Claims, 12 Drawing Sheets

(51) Int. Cl.
*G06T 19/20* (2011.01)
*G16H 30/40* (2018.01)

(56) References Cited

U.S. PATENT DOCUMENTS

| | | | |
|---|---|---|---|
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 2002/0015934 A1* | 2/2002 | Rubbert ............... A61C 7/146 |
| | | 433/29 |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2007/0238065 A1* | 10/2007 | Sherwood ............ A61C 7/08 |
| | | 433/24 |
| 2008/0280247 A1* | 11/2008 | Sachdeva ............. A61C 7/00 |
| | | 703/11 |
| 2008/0305451 A1* | 12/2008 | Kitching ............. A61C 7/00 |
| | | 433/24 |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2013/0231899 A1* | 9/2013 | Khardekar ........... G06F 30/00 |
| | | 703/1 |
| 2014/0247260 A1* | 9/2014 | Ghoneima ........... G06T 19/00 |
| | | 345/419 |
| 2015/0320320 A1* | 11/2015 | Kopelman ........... A61B 6/032 |
| | | 433/215 |
| 2016/0135925 A1* | 5/2016 | Mason ................. A61C 7/002 |
| | | 703/2 |
| 2016/0242870 A1 | 8/2016 | Matov et al. |
| 2016/0310235 A1 | 10/2016 | Derakhshan et al. |
| 2017/0273760 A1 | 9/2017 | Morton et al. |
| 2018/0028063 A1* | 2/2018 | Elbaz ................... H04N 13/271 |
| 2018/0042698 A1* | 2/2018 | Salah ................... G06T 17/00 |
| 2018/0280118 A1 | 10/2018 | Cramer |
| 2019/0008446 A1* | 1/2019 | Cunliffe ............... A61B 5/1078 |
| 2019/0026598 A1* | 1/2019 | Salah ................... A61B 5/0088 |
| 2019/0029784 A1 | 1/2019 | Moalem et al. |
| 2019/0053876 A1 | 2/2019 | Sterental et al. |
| 2019/0125493 A1* | 5/2019 | Salah ................... A61C 7/002 |
| 2019/0192259 A1 | 6/2019 | Kopelman et al. |
| 2019/0328487 A1 | 10/2019 | Levin et al. |

(56) References Cited

U.S. PATENT DOCUMENTS

| | | |
|---|---|---|
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0085546 A1 | 3/2020 | Li et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0174477 A1 | 6/2021 | Shi et al. |
| 2021/0200188 A1* | 7/2021 | Shah ................. G06T 19/20 |
| 2022/0122264 A1* | 4/2022 | Reynard ............. A61B 6/032 |
| 2022/0148263 A1* | 5/2022 | Vannahme ............. G06T 7/11 |
| 2023/0298179 A1* | 9/2023 | Kang ................. G06T 7/73 |
| | | 382/128 |

* cited by examiner

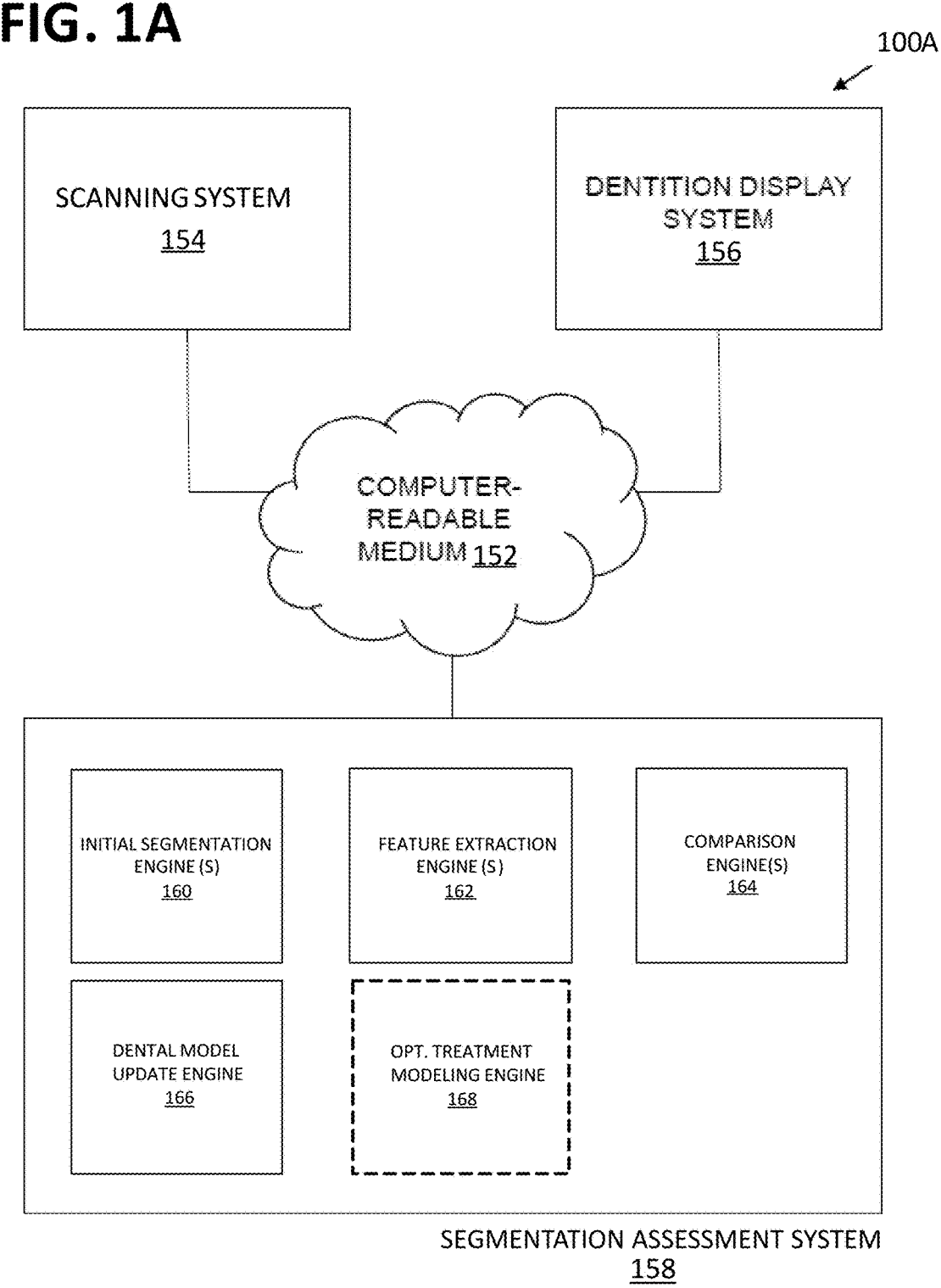

301

FIG. 3G
FIG. 3H
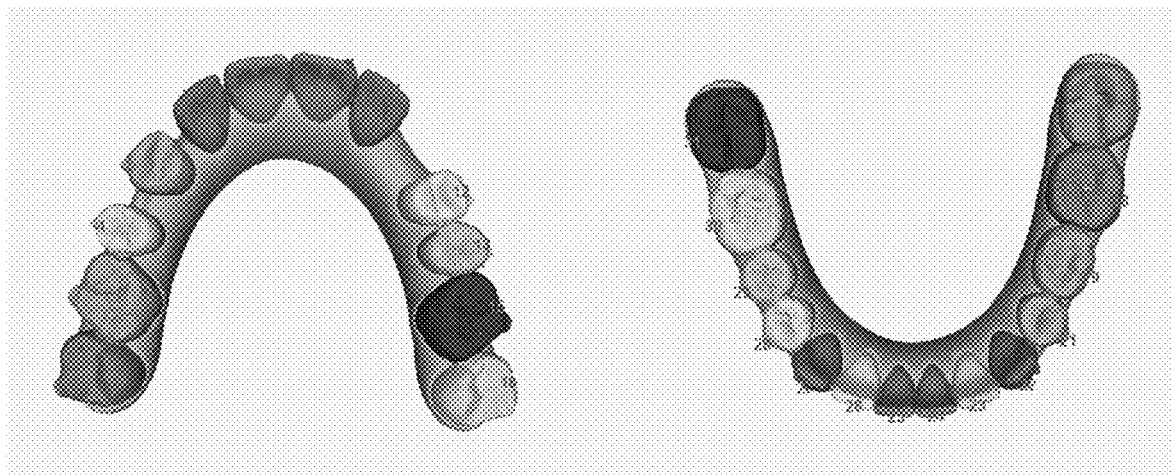
FIG. 3I
FIG. 3J
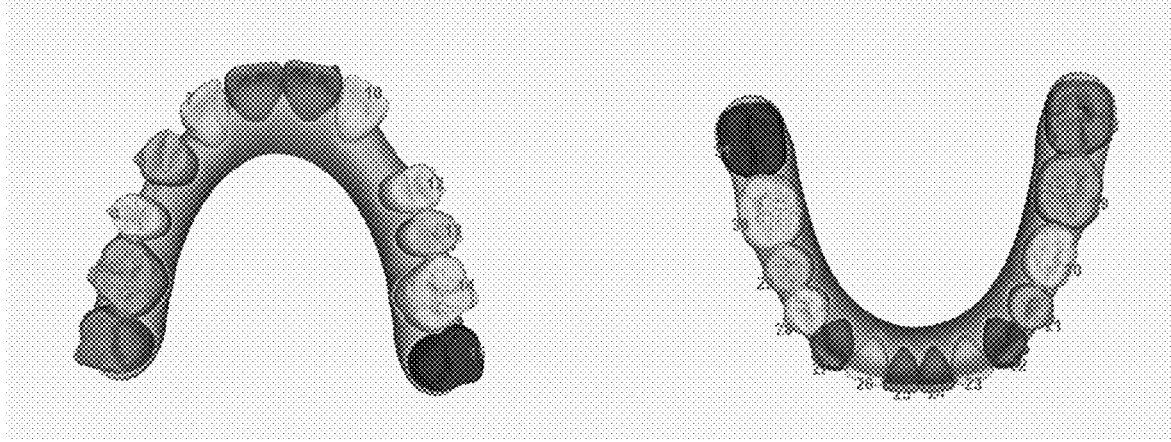

AUTOMATIC SEGMENTATION QUALITY ASSESSMENT FOR SECONDARY TREATMENT PLANS

CROSS REFERENCE TO RELATED APPLICATIONS

This patent application claims priority to U.S. Provisional Patent Application No. 63/077,181, titled "AUTOMATIC SEGMENTATION QUALITY ASSESSMENT FOR SECONDARY TREATMENT PLANS," filed on Sep. 11, 2020, herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Orthodontic procedures typically involve repositioning a subject's teeth to a desired arrangement in order to correct malocclusions and/or improve aesthetics. To achieve these objectives, orthodontic appliances such as braces, shell aligners, and the like can be applied to the subject's teeth by an orthodontic practitioner and/or by the subjects themselves. The appliance can be configured to exert force on one or more teeth in order to effect desired tooth movements according to a treatment plan.

Orthodontic aligners may include devices that are removable and/or replaceable over the teeth. Orthodontic aligners may be provided as part of an orthodontic treatment plan. In some orthodontic treatment plans involving removable and/or replaceable aligners, a subject may be provided plurality of orthodontic aligners over the course of treatment to make incremental position adjustments to the subject's teeth. An orthodontic aligner may have a polymeric trough with an inner cavity shaped to receive and resiliently reposition teeth from one tooth arrangement to a successive tooth arrangement. Orthodontic aligners may include "active" regions that impose repositioning forces on teeth and "passive" regions that retain teeth in their current state.

Some orthodontic aligners make use of a 3D model of the patient's teeth for treatment planning and tracking. The 3D modeling process can include scanning the patient's teeth with an intraoral scanner, generating a 3D model from the scanned data, and segmenting the 3D model to identify individual teeth and/or other intraoral features such as gingiva. Segmentation of 3D models is a complex computational process which can include separating teeth anatomy from gingiva and removing extra material and distortions from the scan. The result of the segmentation significantly affects treatment quality, and poor segmentation results can cause aligner fit issues, pain, and other customer complaints. To improve segmentation outcomes, automatically segmented scans can be manually reviewed and corrected by dedicated person, such as a DDT CAD designer, who can spend time to review and correct segmented dental models, further adding time and expense to orthodontic treatments.

There is a need for accurate, automated segmentation of scans of patients who previously were treated ("primary orders") and have now been scanned again.

SUMMARY OF THE DISCLOSURE

Implementations address the need to improve the accuracy and efficiency of automatic dental model generation and segmentation. The present application addresses these and other technical problems by providing technical solutions and/or automated agents that automatically generate segmented dental models in situations where the patient has previously undergone a dental or orthodontic treatment.

In general, example apparatuses (e.g., devices, systems, etc.) and/or methods described herein may acquire a representation of a subject's teeth. The representation may be digital scan or a 3D model of the subject's teeth. As used herein, a subject may be a patient with or without a diagnosed ailment (e.g., an orthodontic patient, a dental patient, etc.). The methods and apparatuses (e.g., systems) described herein may be used for developing or refining a treatment plan for a subject (e.g., a patient).

Any of the apparatuses and/or methods described herein may be part of a distal tooth scanning apparatus or method, or may be configured to work with a digital scanning apparatus or method.

In some implementations, the 3D model can include automatic tooth segmentation that may provide the basis for implementation of automated orthodontic treatment plans, design and/or manufacture of orthodontic aligners (including series of polymeric orthodontic aligners that provide forces to correct malocclusions in a subject's teeth). These apparatuses and/or methods may provide or modify a treatment plan, including an orthodontic treatment plan. The apparatuses and/or methods described herein may provide instructions to generate and/or may generate a set or series of aligners, and/or orthodontic treatment plans using orthodontic aligners that incorporate post-treatment tooth position scoring. The apparatuses and/or methods described herein may provide a visual representation of the subject's post-treatment tooth positions.

For example, described herein are methods for generating and segmenting a 3D dental model of a subject's dentition, the method comprising: receiving a dental scan of the subject's dentition; determining if the subject has previously undergone dental or orthodontic treatment; and if the subject has previously undergone a dental or orthodontic treatment: generating an initial segmented dental model from the dental scan; obtaining a prior dental model from the subject's previous dental or orthodontic treatment; comparing dentition similarity criteria between the initial segmented dental model and the prior dental model; and modifying the initial segmented dental model with one or more features of the initial segmented dental model based on the comparison of dentition similarly criteria to produce an updated dental model.

In any of these methods, modifying the initial segmented dental model may include using one or more feature of the initial segmented dental model when the comparison of dentition similarly criteria is less than a threshold valve. For example, comparing the dentition similarity criteria may comprise comparing dentition criteria that are correlated to the one or more features of the initial segmented dental model. The one or more features of the initial segmented dental model may include: a tooth axis, a region of a tooth surface, a facial axis of a clinical crown, or a tooth number.

Determining if the subject has previously undergone dental or orthodontic treatment may include searching a historical treatment database with non-scan information.

If the subject has not previously undergone dental or orthodontic treatment, the method may instead include proceeding with a traditional dental modeling and segmentation process that includes a manual quality control check by a trained professional.

In any of these methods, the initial segmented dental model may comprise a 3D dental mesh model. The prior dental model may be a final 3D model from the subject's previous dental or orthodontic treatment.

The dentition similarity criteria may be based on multiple treatment plan parameters that were applied during the subject's previous dental or orthodontic treatment. For example, the dentition similarity criteria may be one or more of an overall number of teeth, a tooth geometry in different areas, teeth numeration, or a number of treated jaws. In some examples the dentition similarity criteria are references representing tooth shape similarity from the subject's previous dental or orthodontic treatment. The dentition similarity criteria may be references representing expected tooth motion trajectory from the subject's previous dental or orthodontic treatment.

In general, comparing the dentition similarity criteria may include calculating a rigid transformation of teeth in the initial segmented dental model having references matching shapes to corresponding teeth in the prior dental model. Modifying the initial segmented dental model may further include inferring positions and/or forms of teeth from the prior dental model. For example, modifying the initial segmented dental model may further include restoring missing anatomy with shape data from the prior dental model.

In some examples, modifying the initial segmented dental model may include updating teeth axes with axes data from the prior dental model. Modifying the initial segmented dental model may further comprise performing initial tooth matching using teeth relative positions between the initial segmented dental model and the prior dental model. Modifying the initial segmented dental model may include performing precise tooth matching using geometric tooth features between the initial segmented dental model and the prior dental model. Modifying the initial segmented dental model may include removing interproximal area collisions in the initial segmented dental model based on the prior dental model.

Modifying the initial segmented dental model may include correcting tooth shapes and gingival lines using borders based on the prior dental model. In some examples modifying the initial segmented dental model further comprises enumerating the initial segmented dental model with a numeration of the prior dental model.

Any of these methods may include automatically trimming the updated dental model based on a trim line of the prior dental model.

Also described herein are apparatuses (including software, hardware and/or firmware) for performing any of the methods described herein. In particular, described herein are non-transitory computer-readable medium including contents that are configured to cause one or more processors to perform a method comprising: receiving a dental scan of a subject's dentition; determining if the subject has previously undergone dental or orthodontic treatment; and if the subject has previously undergone dental or orthodontic treatment: generating an initial segmented dental model from the dental scan; obtaining a prior dental model from the subject's previous dental or orthodontic treatment; comparing dentition similarity criteria between the initial segmented dental model and the prior dental model; and modifying the initial segmented dental model with one or more features of the initial segmented dental model based on the comparison of dentition similarly criteria to produce an updated dental model.

An of these methods and apparatuses may include locking in the regions or features (e.g., surface regions, segmentation, axes, numbering, etc.) of the model (in an updated model, for example) that are verified by comparison between the prior digital model and the current digital model. Thus, the methods or apparatus may include one or more user interfaces that are configured to prevent the user from modifying these verified features.

For example, described herein are non-transitory computer-readable medium including contents that are configured to cause one or more processors to perform a method comprising: generating an initial segmented dental model from a dental scan of a subject's dentition; comparing dentition similarity criteria between the initial segmented dental model and a prior dental model; and modifying the initial segmented dental model with one or more features from the initial segmented dental model based on the comparison of dentition similarly criteria to produce an updated dental model; displaying the updated dental model in which the one or more features from the initial segmented dental model are marked; and permitting a user to modify the updated dental model from the display, but preventing the user from modifying the marked one or more features from the initial segmented dental model.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is a diagram showing an example of a computing environment configured to digitally scan a dental arch and determine a post-treatment tooth position score.

FIGS. 3A-3J illustrate one implementation of the method described in FIG. 2.

DETAILED DESCRIPTION

Figure 1B:
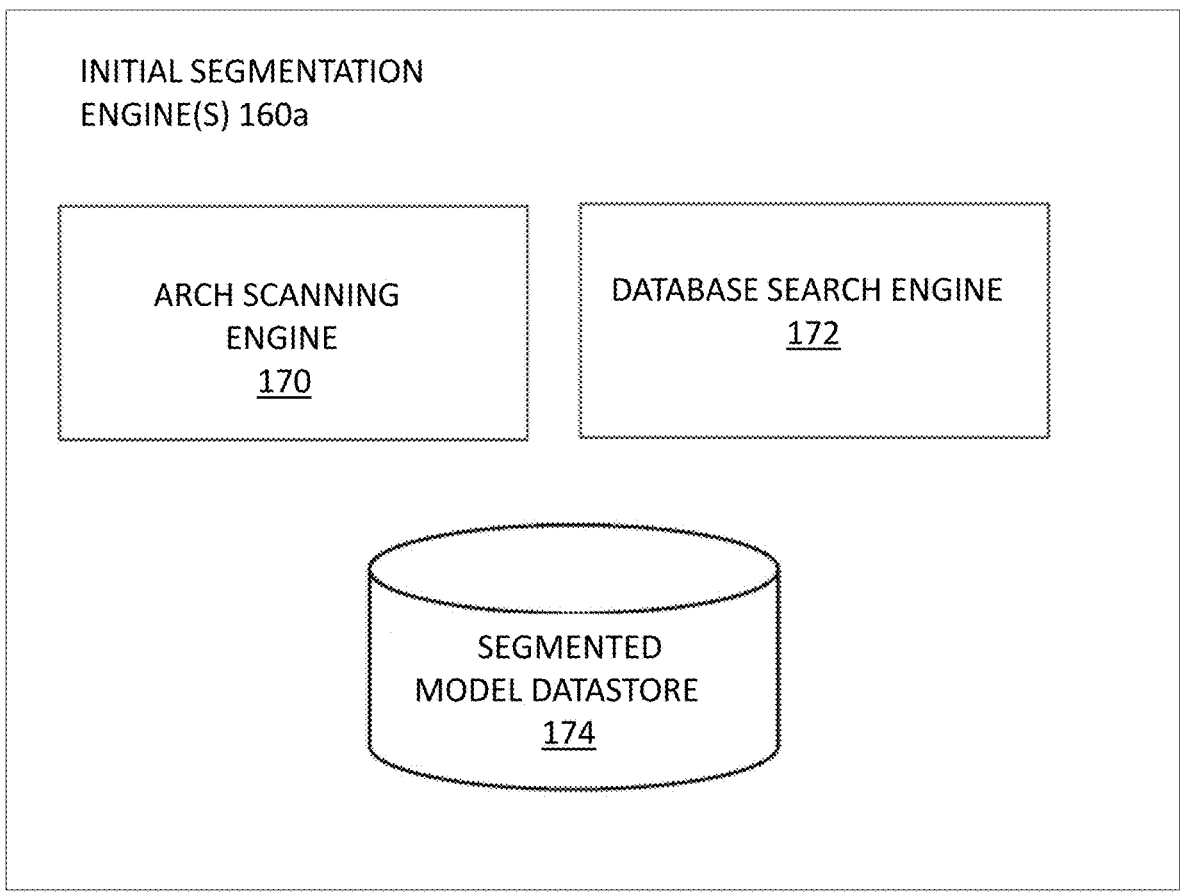
FIG. 1B is a diagram showing an example of an initial segmentation engine(s).

Described herein are apparatuses (e.g., systems, computing device readable media, devices, etc.) and methods for improving automated segmentation outcomes of 2D or 3D dental models. In some implementations, the apparatuses and methods described herein can utilize data from a patient's prior treatment plan to assess and/or improve the quality of segmentation of a new 3D dental model in a subsequent treatment. For example, prior treatment plan data such as a prior 3D dental model can be compared against the new 3D dental model to determine the segmentation quality of the new 3D dental model. Additionally, apparatuses and methods described herein can supplement this new 3D dental model with the prior 3D dental model to improve the accuracy of the new 3D dental model.

The apparatuses and/or methods described herein may be useful in planning and fabrication of dental appliances, including elastic polymeric positioning appliances, is described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., San Jose, Calif., under the tradename, Invisalign System.

Throughout the body of the Description of Embodiments, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

An "subject," as used herein, may be any subject (e.g., human, non-human, adult, child, etc.) and may be alternatively and equivalently referred to herein as a "patient", a "patient under treatment", or a "subject." A "patient," as used herein, may but need not be a medical patient. An "subject" or a "patient," as used herein, may include a person who receives orthodontic treatment, including orthodontic treatment with a series of orthodontic aligners.

As described herein, any of a variety of tools can be used to convert a "real world" representation of a patient's dentition into a virtual model. For example, an image (e.g., picture or scan) of the dentition can be converted to a 2D or 3D model (e.g., 2D or 3D mesh). In some cases, a number of images are combined to create a single model. In some examples, an intraoral scanner generates multiple different images of a dental site, model of a dental site, or other object. The images may be discrete images (e.g., point-and-shoot images) or frames from a video (e.g., a continuous scan). The intraoral scanner may automatically generate a 3D model of the patient's teeth. In some cases, the 3D model includes the digital detailing and cut and detail processes during which a 3D mesh is converted into a CAD model with labeled teeth.

In a number of systems, a digital representation of a dental arch is partitioned into constituent parts, including teeth. This process is sometimes referred to segmentation or auto-segmentation. The teeth are then identified and numbered according to their dental tooth type. The tooth numbering may be used to create a treatment plan for correcting teeth locations. The process for both 2D images and 3D meshes generally begins by identifying which objects in the representation correspond to the central incisors and then working distally to identify the tooth number corresponding to the other objects. This process may cause errors in numbering if there are missing teeth and/or supernumerary teeth. For example, if a patient is missing their first premolars, then the system may mislabel the second premolars as first premolars and the first molars as second premolars. This is particularly likely when the patient's teeth differ from the norm.

As described herein, an intraoral scanner may image a subject's dental arch and generate a virtual three-dimensional model of that dental arch. During an intraoral scan procedure (also referred to as a scan session), a user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan).

FIG. 1A is a diagram showing an example of a computing environment 100A configured to facilitate gathering and processing digital scans of a dental arch with teeth therein. The environment 100A includes a computer-readable medium 152, a scanning system 154, a dentition display system 156, and a segmentation assessment system 158. One or more of the modules in the computing environment 100A may be coupled to one another or to modules not explicitly shown.

The computer-readable medium 152 and other computer readable media discussed herein are intended to represent a variety of potentially applicable technologies. For example, the computer-readable medium 152 can be used to form a network or part of a network. Where two components are co-located on a device, the computer-readable medium 152 can include a bus or other data conduit or plane. Where a first component is co-located on one device and a second component is located on a different device, the computer-readable medium 152 can include a wireless or wired back-end network or LAN. The computer-readable medium 152 can also encompass a relevant portion of a WAN or other network, if applicable.

The scanning system 154 may include a computer system configured to scan a subject's dental arch. A "dental arch," as used herein, may include at least a portion of a subject's dentition formed by the subject's maxillary and/or mandibular teeth, when viewed from an occlusal perspective. A dental arch may include one or more maxillary or mandibular teeth of a subject, such as all teeth on the maxilla or mandible or a subject. The scanning system 154 may include memory, one or more processors, and/or sensors to detect contours on a subject's dental arch. The scanning system 154 may be implemented as a camera, an intraoral scanner, an x-ray device, an infrared device, etc. In some implementations, the scanning system 154 is configured to produce 3D scans of the subject's dentition. In other implementations the scanning system 154 is configured to produce 2D scans or images of the subject's dentition. The scanning system 154 may include a system configured to provide a virtual representation of a physical mold of patient's dental arch. The scanning system 154 may be used as part of an orthodontic treatment plan. In some implementations, the scanning system 154 is configured to capture a subject's dental arch at a beginning stage, an intermediate stage, etc. of an orthodontic treatment plan. The scanning system 154 may be further configured to receive 2D or 3D scan data taken previously or by another system.

The dentition display system 156 may include a computer system configured to display at least a portion of a dentition of a subject. The dentition display system 154 may include memory, one or more processors, and a display device to display the subject's dentition. The dentition display system 156 may be implemented as part of a computer system, a display of a dedicated intraoral scanner, etc. In some implementations, the dentition display system 156 facilitates display of a subject's dentition using scans that are taken at an earlier date and/or at a remote location. It is noted the dentition display system 156 may facilitate display of scans taken contemporaneously and/or locally to it as well. As noted herein, the dentition display system 156 may be configured to display the intended or actual results of an orthodontic treatment plan applied to a dental arch scanned by the scanning system 154. The results may include 3D virtual representations of the dental arch, 2D images or renditions of the dental arch, etc.

The segmentation assessment system 158 may include a computer system, including memory and one or more processors, configured to assess and improve the quality and accuracy of a 3D dental model of a patient's dentition, particularly when the patient has undergone a prior orthodontic treatment. In one implementation, the segmentation assessment system is configured to process scan data from the scanning system 154. In some examples, 2D or 3D scan data, may be processed to generate a 3D dental model or 3D dental mesh. The segmentation assessment system may be further configured extract relevant information from the 3D dental model, such as upper/lower jaw masking, tooth segmentation information including tooth numbering, and/or tooth edge information. In one implementation, the segmentation assessment system may be configured to determine if the patient has previously undergone orthodontic treatment, and can be configured to access data from the prior treatment such as prior 3D dental models and dental treatment plans. The segmentation assessment system can be configured to identify dentition similarity criteria from the 3D dental model and the prior 3D dental model(s) and compare the 3D dental models to assess the quality of the 3D dental model, including the quality of segmentation of individual teeth in the 3D dental model. In further implementations, the segmentation assessment system may be configured to supplement, modify, and/or update the 3D dental model with data and/or features from the prior 3D dental model(s). The segmentation assessment system 158 may include initial segmentation engine(s) 160, feature extraction engine(s) 162, comparison engine(s) 164, dental model update engine(s) 166, and optional treatment modeling engine(s) 168. One or more of the modules of the segmentation assessment system 158 may be coupled to each other or to modules not shown.

The initial segmentation engine(s) 160 of the segmentation assessment system 158 may implement automated agents to configured to process tooth scans from the scanning system 154. The initial segmentation engine(s) 160 may include graphics engines to process images or scans of a dental arch. In some implementations, the initial segmentation engine(s) 160 is configured to format scan data from a scan of a dental arch into a dental mesh model (e.g., a 3D dental mesh model) of the dental arch. The initial segmentation engine(s) 160 may also be configured to segment the 3D dental mesh model of the dental arch into individual dental components, including segmenting the 3D dental mesh model into 3D mesh models of individual teeth. During segmentation, the initial segmentation engine(s) 160 may be configured to automatically and accurately label the teeth of the 3D dental model, e.g., by numbering the teeth in a standard tooth numbering. The 3D dental mesh models of the dental arch and/or the individual teeth may comprise geometric point clouds or polyhedral objects that depict teeth and/or other elements of the dental arch in a format that can be rendered on the dentition display system 156. In some embodiments, the 3D dental mesh models of the dental arch and/or the individual teeth can be rendered into a 2D image. The 3D dental models may include 3D tooth shape representations in the form of a tooth point cloud, a tooth mesh, or a reduced parameter representation.

In one implementation, the initial segmentation engine(s) 160 may be further configured to determine if the patient has previously undergone orthodontic treatment. For example, the initial segmentation engine(s) 160 can be configured to access non-scan information, such as personal information, that allows for searching in a historical database of treatments for prior treatment data. If the patient has a prior treatment history, the initial segmentation engine(s) 160 can be configured to access data from the prior treatment, such as prior 3D dental models and dental treatment plans. The prior 3D dental models and/or prior dental treatment plans are digital representations of the patient's teeth at a prior time. For example, the prior 3D dental model can be a final 3D model from a prior dental treatment. In other implementations, the prior 3D dental model can be an intermediate 3D dental model or an initial 3D dental model from the prior dental treatment. As used herein, a "3D dental model" or "3D dental mesh model" that is created by the initial segmentation engine(s) 160 may refer to a new or current dental model of a patient's dentition, and a "prior 3D dental model" or "prior 3D dental mesh model" may refer to a dental model of the patient's dentition that was previously created for a prior dental treatment. The initial segmentation engine(s) 160 may provide 3D dental mesh models, prior 3D dental mesh models, prior treatment plans, and/or other data to other modules of the segmentation assessment system 158.

The feature extraction engine(s) 162 of the segmentation assessment system 158 may implement one or more automated agents configured to extract dental features or dentition similarity criteria from the 3D dental mesh model, prior 3D dental mesh models, and/or from prior treatment plans. A "dental feature" or "dentition similarity criteria," as used herein, may include data points from the 3D dental mesh model or the prior 3D dental mesh model(s) that correlate to shapes, positions, orientations, edges, contours, vertices, vectors, or surfaces of the patient's teeth. In some examples, a "dental feature" or "dentition similarity criteria" may be based on multiple treatment plan parameters that were applied during a prior treatment plan. A "dental feature" or "dentition similarity criteria" may further include the overall number of teeth in the patient's dentition, tooth geometry in different areas of the patient's dentition, teeth numeration, and the number of treated jaws in the patient's dentition. Additionally, a "dental feature" or "dentition similarity criteria" may further include data representing expected tooth/teeth motion trajectory from prior treatment plans. In some implementations, the feature extraction engine(s) 162 is configured to analyze 3D dental mesh models or the prior 3D dental models from the initial segmentation engine(s) 160 to extract the dental features or dentition similarity criteria. In one implementation, the feature extraction engine(s) 162 may, for each tooth in the 3D dental model, extract a subset of dental features from the 3D dental mesh model or the prior 3D dental model. For example, a specified number of tooth measurement points (e.g., nine tooth measurement points) can be extracted. This subset of measurement points can be selected to define the position and orientation of each tooth, as well as partial information on the tooth shape. The feature extraction engine(s) 162 may provide dental features, dentition similarity criteria, and/or other data to other modules of the segmentation assessment system 158.

The comparison engine(s) 164 of the segmentation assessment system 158 may implement one or more automated agents configured to compare the segmentation results of the 3D dental model with the segmentation results of a prior 3D dental model or prior treatment plan. For example, the comparison engine(s) 164 may receive dental features or dentition similarity criteria from the feature extraction engine(s) 162. The dental features or dentition similarity criteria can include features from the 3D dental model and from the prior 3D dental model(s) or prior treatment plans. In one implementation, the comparison engine(s) 164 is further configured to compare the dentition similarity criteria from the 3D dental model to one or more of the prior 3D dental models to produce comparison data. The comparison data can be used to determine if the dental features or dentition similarity criteria of individual teeth (e.g., such as shape, position, or orientation) in the 3D dental model are within an acceptable threshold of corresponding dental features or dentition similarity criteria in the prior 3D dental model(s). The comparison engine(s) 164 can be configured to assess the quality of the 3D dental model, including the quality of the segmentation of individual teeth based on the comparison between the 3D dental model and prior 3D dental models.

The dental model update engine(s) 166 of the segmentation assessment system 158 may implement one or more automated agents configured to supplement or update the 3D dental model with data from the prior 3D dental models or treatment plans, such as with the dentition similarity criteria. For example, the dental model update engine can be configured to restoring missing anatomy in scan hole areas by importing shape data from prior 3D dental models. The dental model update engine(s) 166 can be further configured to use tooth shape data, tooth position data, and/or tooth orientation data from prior 3D dental models to improve detection, identification, and formation of teeth models of individual teeth during segmentation of the 3D dental model. Furthermore, the dental model update engine can implement one or more automated agents configured to use prior 3D dental model data to remove collisions between adjacent modeled teeth in interproximal areas of the 3D dental model, create a gingiva model in the 3D dental model, and number/enumerate the segmented 3D dental model, including accommodating for missing teeth and/or unusual spatial configurations.

The optional treatment modeling engine(s) 168 may be configured to use the 3D model to store and/or provide instructions to implement orthodontic treatment plans and/or the results of orthodontic treatment plans. The optional treatment modeling engine(s) 168 may provide the results of orthodontic treatment plans on the 3D dental model. In some embodiments, the 3D dental model can be rendered into one or more 2D image(s) from a plurality of viewing angles. The optional treatment modeling engine(s) 168 may model the results of application of orthodontic aligners to the subject's dental arch over the course of an orthodontic treatment plan.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud based datastore is a datastore that is compatible with cloud-based computing systems and engines.

FIG. 1B is a diagram showing an example of the segmentation engine(s) 160*a*. The segmentation engine(s) 160*a* may include an arch scanning engine 170, a database search engine 172, and a segmented model datastore 174. One or more of the modules of the segmentation engine(s) 160*a* may be coupled to each other or to modules not shown.

The arch scanning engine 170 may implement one or more automated agents configured to scan a 3D dental mesh model for individual tooth segmentation data. "Individual tooth segmentation data," as used herein, may include shapes, positions, orientations, geometrical properties (contours, etc.), and/or other data that can form the basis of segmenting individual teeth from 3D or 2D dental mesh models of a patient's dental arch. The arch scanning engine 168 may implement automated agents to separate dental mesh data for individual teeth from a 3D or 2D dental mesh model of the dental arch. The arch scanning engine 168 may further implement automated agents to number the individual teeth within the 3D dental model.

The database search engine 172 may implement one or more automated agents configured to determine if the patient has previously undergone a dental or orthodontic treatment. A prior orthodontic treatment can include, for example, previously scanning the patient's dentition, previously generating a prior 3D dental model of the patient's dentition, and/or previously repositioning the patient's teeth to a desired arrangement with orthodontic aligners. In one implementation, the database search engine can implement one or more automated agents to obtain non-scan information to allow for searching in a historical database of treatments for prior treatment data. The non-scan information can comprise, for example, personal information such as the patient's name, phone number, DOB, address, patient number, etc. that would allow for lookup of a prior treatment. The searchable historical database can include all relevant data and information relating to the prior treatment(s), including prior 3D dental models, prior treatment plans, and segmentation data associated with the prior 3D dental models. If the database search engine determines that the patient has not undergone a prior dental or orthodontic treatment, then the database search engine 172 can provide an instruction or recommendation for the 3D dental model generated by the arch scanning engine 170 to undergo a traditional quality control process to evaluate the quality of the model. The traditional quality control process can include, for example, manual review of the 3D dental model by a trained technician.

The segmented model datastore 174 may be configured to store data related to model dental arches, including the 3D dental model that has been segmented into individual teeth. The model dental arch data may comprise data related to segmented individual teeth, including tooth identifiers of the individual teeth such as tooth types and tooth numbers. The segmented model datastore 174 may be further configured to store data related to prior treatments of the patient, including prior 3D dental models (including segmentation data) and prior treatment plans.

Figure 1C:
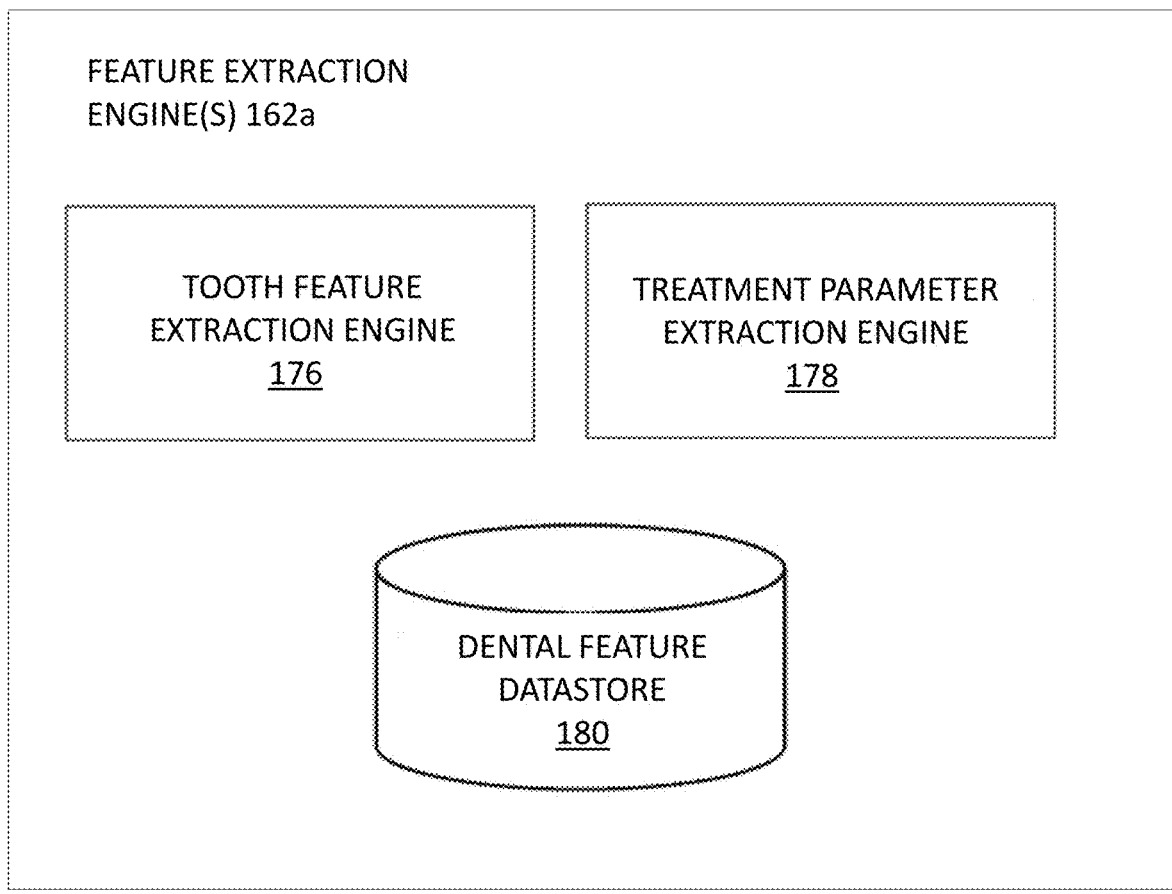
FIG. 1C is a diagram showing an example a feature extraction engine(s).

FIG. 1C is a diagram showing an example of a feature extraction engine(s) 162*a*. The feature extraction engine(s) 162*a* may include a tooth feature extraction engine 176, a treatment parameter extraction engine 178, and a dental feature datastore 180. One or more of the modules of the feature extraction engine(s) 162*a* may be coupled to each other or to modules not shown.

The tooth feature extraction engine 176 may implement one or more automated agents configured to determine or extract dental features or dentition similarity criteria from the 3D dental model (e.g., the current or new 3D dental model) and from the prior 3D dental models or treatment plans. The tooth feature extraction engine can be configured to extract dental features related to the shape, position, and/or orientation of teeth in the 3D dental model and the prior 3D dental models. These dental features can comprise, for example, shapes, positions, orientations, edges, contours, vertices, vectors, or surfaces of the patient's teeth, the overall number of teeth in the patient's dentition, tooth geometry in different areas of the patient's dentition, and teeth numeration.

The treatment parameter feature extraction engine 178 may implement one or more automated agents configured to determine or extract dental features or dentition similarity criteria from the 3D dental model (e.g., the current or new 3D dental model) and from the prior 3D dental models or treatment plans. The treatment parameter extraction engine can be configured to extract dental features related to current and prior orthodontic or dental treatments of the patient. These dental features can comprise, for example, the number of currently and previously treated jaws in the patient's dentition, treatment plan parameters including tooth repositioning/trajectory parameters, and expected tooth/teeth trajectory data.

The dental feature datastore 180 may be configured to store data related to the extracted dental features or dentition similarity criteria, including features related to the tooth shape, position, and/or orientation (from the tooth feature extraction engine) and features related to current and prior treatments (from the treatment parameter extraction engine).

Figure 1D:
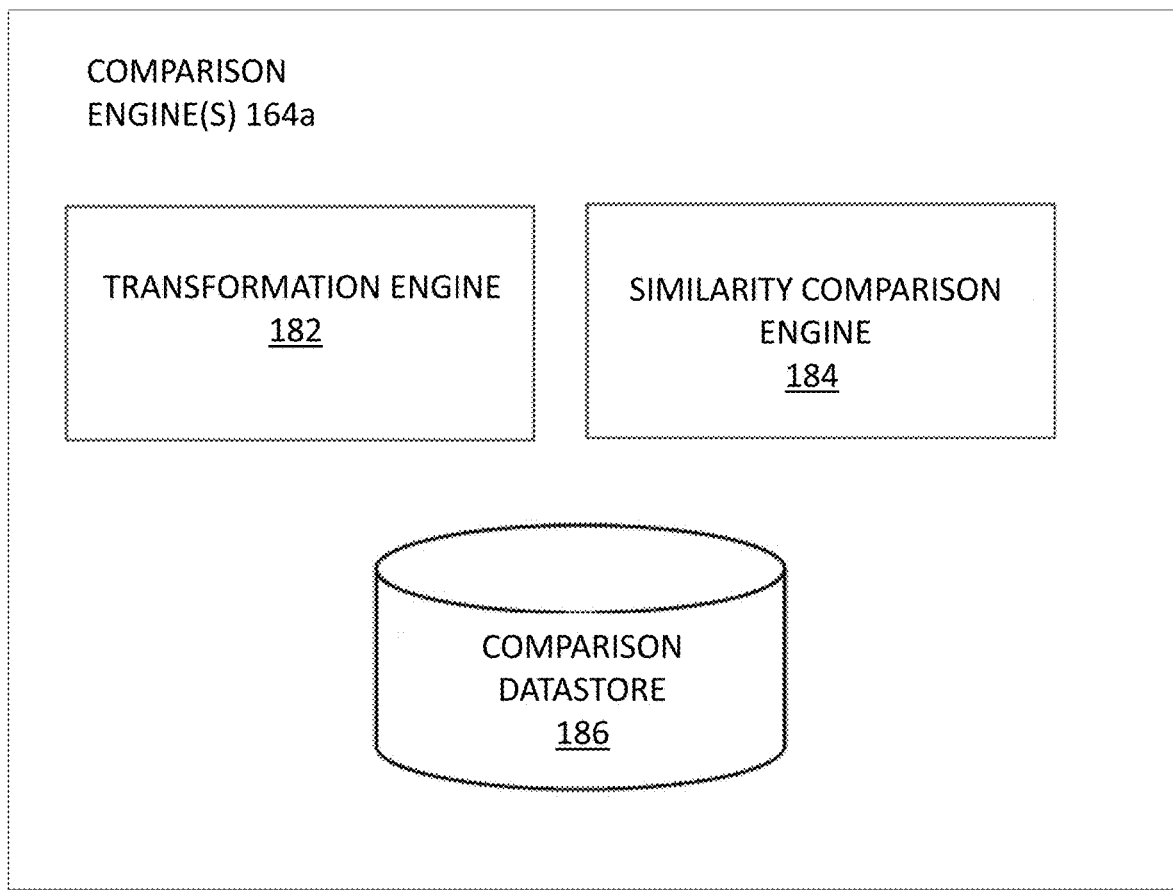
FIG. 1D is a diagram showing an example of a comparison engine(s).

FIG. 1D is a diagram showing an example of a comparison engine(s) 164*a*. The comparison engine(s) 164*a* may include a transformation engine 182, a similarity comparison engine 184, and a comparison datastore 186. One or more of the modules of the comparison engine(s) 164*a* may be coupled to each other or to modules not shown.

The transformation engine 182 may implement one or more automated agents configured to correlate extracted features or dentition similarity criteria from the 3D dental model (e.g., the current or new 3D dental model) to extracted features or dentition similarity criteria from the prior 3D dental models or treatment plans. For example, the transformation engine 182 can match the extracted dental features related to the shape, position, and/or orientation of teeth in the 3D dental model to the extracted dental features related to the shape, position, and/or orientation of teeth in the prior 3D dental models. In one implementation, the transformation engine can calculate a rigid transformation of teeth which have extracted features from both the 3D dental model and the prior 3D dental model to match the shapes of the teeth in the current 3D dental model to the shapes of the teeth in the prior 3D dental model. Additionally, in one implementation the transformation engine 182 can use tooth forms/positions from prior 3D dental models to improve tooth detection in the new 3D dental model. For example, visible crown borders can be identified in both the current and prior 3D dental models to identify/number the individual teeth in the new 3D dental model.

The similarity comparison engine 184 may implement one or more automated agents configured to access the quality of the segmentation result of the current 3D dental model. initially, the similarity comparison engine 184 may compare extracted features from the 3D dental model to corresponding extracted features from the prior 3D dental model(s) to determine if the current 3D dental model is similar enough to the prior 3D dental model to bypass traditional quality control processes. For example, the overall number of teeth in the 3D dental model can be compared to the overall number of teeth in the prior 3D dental models, the tooth geometry in different areas or regions of the dental arch in the 3D dental model can be compared to the tooth geometry in different areas or regions of the dental arch in the prior 3D dental models, the teeth numeration in the 3D dental model can be compared to the teeth numeration in the prior 3D dental models, and/or the number of treated jaws in the 3D dental model can be compared to the number of treated jaws in the prior 3D dental model(s). In one implementation, the similarity comparison engine 184 can further compare the shapes of the individual teeth in the 3D dental model to the shapes of corresponding individual teeth in the prior 3D dental model(s). For example, the 2D and/or 3D dimensions of each tooth can be compared to the 2D and/or 3D dimensions of each corresponding tooth, and the similarity comparison engine 184 can determine if the shape of each tooth in the 3D dental model falls within an acceptable threshold when compared to the shape of its corresponding tooth from the prior 3D dental models. The comparison of any and all of the extracted features described above can be used by the comparison engine to determine or assess the quality of the segmentation of the 3D dental model. If, for example, the comparisons are within an acceptable threshold, then the segmentation can be deemed to be acceptable. Alternatively, if the comparison falls outside of an acceptable threshold, then the segmentation can be deemed unacceptable, and steps can be taken to either re-scan the patient, re-do the segmentation, or have a trained technician manually segment the 3D dental model.

The comparison datastore 186 may be configured to store data related to the comparison of extracted dental features or dentition similarity criteria, including whether the comparison is within an acceptable threshold. The comparison datastore 186 can be further configured to store data related to any determinations the similarity comparison engine makes based on the quality of the segmentation result of the 3D dental model (i.e., if the segmentation result is acceptable or unacceptable).

Figure 1E:
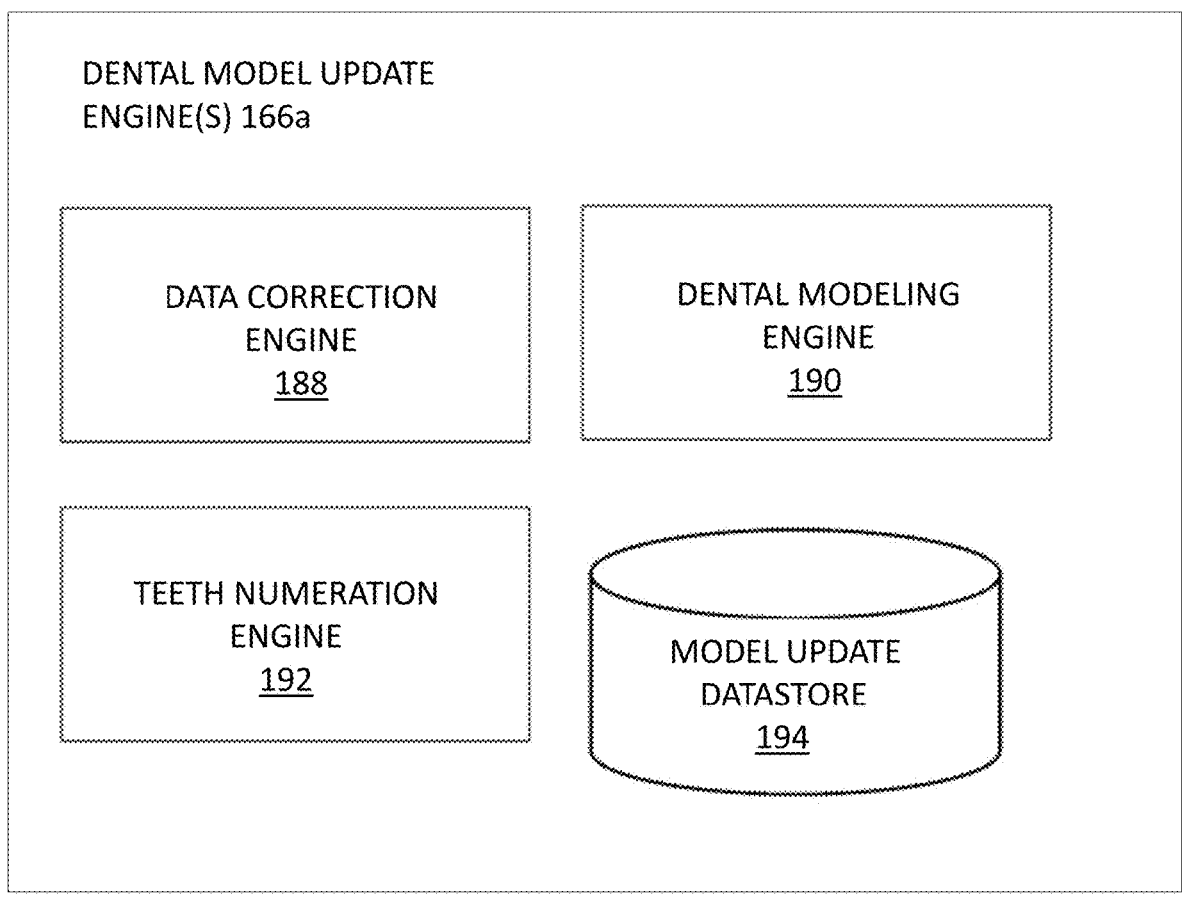
FIG. 1E is a diagram showing an example of dental model update engine(s).

FIG. 1E is a diagram showing an example of a dental model update engine(s) 166a. The dental model update engine(s) 166a may include a data correction engine 188, a dental modeling engine 190, a teeth numeration engine 192, and a model update datastore 194. One or more of the modules of the dental model update engine(s) 166a may be coupled to each other or to modules not shown.

The data correction engine 188 may implement one or more automated agents configured to restore, update, remove, or supplement missing, incomplete, or incorrect data in the 3D dental model. For example, in some implementations, scan data used to create the new 3D dental model may be incomplete or corrupted, resulting in missing anatomy (such as missing teeth) or partial missing anatomy in the 3D dental model. The data correction engine may implement automated agents configured to restore missing anatomy in the new 3D dental model with shape data/anatomy data/3D modeling data from prior 3D dental models. In some implementations, the data correction engine is configured to use tooth shape data from prior 3D dental model(s) to provide more precise calculations of the facial axis of the clinical crown (FACC line) and tooth axes in the new 3D dental model that will be used for final positioning and overall treatment quality. For example, the FACC line and tooth axes from the prior 3D dental models can be used to create borders for clinical crown detection, which can be used to avoid errors in the new 3D dental model with some scan areas wrongly considered as a part of a tooth clinical crown. The data correction engine 188 may further implement one or more automated agents configured to use prior 3D dental model data to remove collisions between adjacent modeled teeth in interproximal areas of the new 3D dental model.

The data modeling engine 192 may implement one or more automated agents configured to use prior 3D dental model(s) to improve detection, identification, and formation of the new 3D dental model, including identification, segmentation, and formation of individual teeth models and gingiva of the 3D dental model. In one implementation, the data modeling engine 192 can implement automated agents configured to perform initial tooth matching by comparing the relative tooth positions of teeth in the new 3D dental model to the relative tooth positions of teeth in prior 3D dental model(s). The data modeling engine 192 can further implement automated agents configured to perform precision tooth matching by comparing geometric tooth features of teeth in the new 3D dental model to the geometric tooth features of teeth in prior 3D dental model(s). The geometric tooth features can comprise, for example, the extracted features or dentition similarity criteria discussed above. In one implementation, the data modeling engine 192 may implement automated agents configured to generate a gingiva model either separate from or incorporated into the 3D dental model. The creation of the gingiva model can be based on tooth shape data, tooth borders, and other information from prior 3D dental models. Additionally, the data modeling engine 192 can be configured to perform automatic trimming (i.e., to determine where an orthodontic aligner will be cut/trimmed in order to fit the patient and effectively move the teeth as desired) based on the prior 3D dental models.

The teeth numeration engine 192 may implement one or more automated agents configured to use prior 3D dental model(s) to number individual teeth in the new 3D dental model. In one implementation, the teeth numeration engine 192 can implement automated agents configured to use the tooth positions and/or shapes of teeth in the new 3D dental model relative to prior 3D dental model(s) to enumerate the teeth in the new 3D dental model. In some examples, a patient may have unusual teeth spatial configurations or missing/extracted teeth, which can make automated tooth numeration difficult. The teeth numeration engine can easily and accurately numerate the teeth in the new 3D dental model based on the prior numeration of the prior 3D dental model(s).

Figure 2:
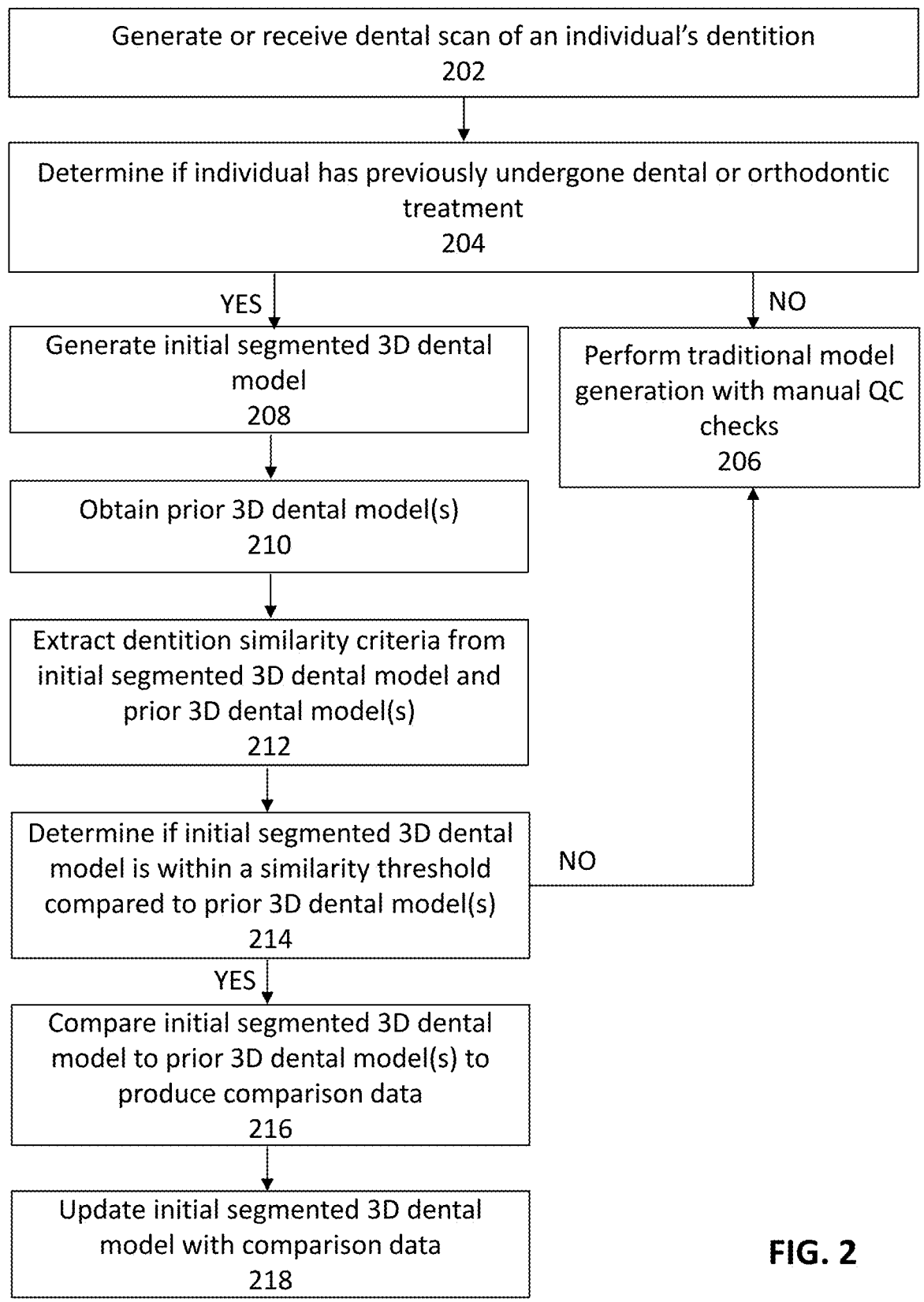
FIG. 2 is a flowchart describing one example of a method of automatically generating and segmenting a 3D dental model of a subject's dentition.

FIG. 2 illustrates a flowchart of a method for automatically generating and segmenting a 3D dental model of a subject's dentition. This method may be automatically implemented by a system, such as one or more of the systems in the computing environment 100A, shown in FIG. 1A.

At an operation 202, the system may automatically generate or receive a dental scan of a subject's dentition. In one implementation, the system may automatically collect a three-dimensional (3D) scan of the patient's dental arch. The 3D scan may be collected directly from the patient (e.g., using an intraoral scanner) or indirectly (e.g., by scanning a mold of the patient's dentition and/or by receiving a digital model of the patient taken by another, etc.).

At an operation 204, the system may automatically determine if the subject has previously undergone a dental or orthodontic treatment. For example, the system may be configured to access non-scan information, such as personal information, that allows for searching a historical database of treatments for prior treatment data of the subject.

At an operation 206, if the system determines that the subject has not previously undergone a dental or orthodontic treatment, the system can initiate and perform a traditional dental model generation process. This process typically includes a hybrid of automated 3D dental model generation, segmentation, and numeration, followed by timely/costly manual quality control checks and confirmation by a trained specialist.

At an operation 208, however, if the system determines that the subject has previously undergone a dental or orthodontic treatment, the system can generate an initial segmented 3D dental model. The scan from operation 202 can be used to generate the initial 3D dental model. The initial 3D dental model may be segmented into individual teeth (and non-teeth elements, such as gingiva, arch, etc.). Additionally, the individual teeth can be numbered according to a standardized tooth numbering system. The initial 3D dental model can comprise a 3D dental mesh model, a 3D point cloud, or a PCA representation, etc.

At an operation 210, the system may automatically obtain data related to the subject's prior dental or orthodontic treatment(s). For example, the patient has a prior treatment history, the system can be configured to access data from the prior treatment, such as prior 3D dental models and dental treatment plans. The prior 3D dental models can represent the subject's teeth at a prior time (e.g., prior to the current treatment).

At an operation 212, the system may automatically extract features or dentition similarity criteria from the initial (or new) 3D dental model and from the prior 3D dental model(s). The features or dentition similarity criteria may include data points from the 3D dental mesh model and/or the prior 3D dental mesh model(s) that correlate to shapes, positions, orientations, edges, contours, vertices, vectors, or surfaces of the subject's teeth. Additionally, the features or dentition similarity criteria may include the overall number of teeth in the patient's dentition, tooth geometry in different areas of the patient's dentition, teeth numeration, the number of treated jaws in the patient's dentition, and expected tooth/teeth motion trajectory from prior treatment plans.

At an operation 214, the system may automatically determine if the initial segmented 3D dental model is within a similarity threshold compared to the prior 3D dental model(s). For example, the system can compare the dentition similarity criteria (from operation 212) from the 3D dental model to one or more of the prior 3D dental models to produce comparison data. The comparison data can be used to determine if the dental features or dentition similarity criteria of individual teeth (e.g., such as shape, position, orientation, number of teeth, number of treated jaws, tooth geometry, etc.) in the initial 3D dental model are within an acceptable threshold of corresponding dental features or dentition similarity criteria in the prior 3D dental model(s). If the initial segmented 3D dental model is not within the similarity threshold, the method can return to operation 206. However, if these features are within the similarity threshold, the traditional QC process of operation 206 can be bypassed, and the method can proceed to operation 216.

At an operation 216, the system can be configured to compare the initial segmented 3D dental model to the prior dental models to produce comparison data. For example, the system can calculate a rigid transformation of teeth which have extracted features from both the 3D dental model and the prior 3D dental model to match the shapes of the teeth in the current 3D dental model to the shapes of the teeth in the prior 3D dental model. The dimensions, shapes, axes, orientation, and position of the subject teeth can be calculated in both the current 3D dental model and the prior 3D dental model can be compared to produce comparison data. The comparison data can include, for example, data indicating the precise differences between the current 3D dental model and the prior 3D dental model(s).

At an operation 218, the system can be configured to update or supplement the initial 3D dental model from the prior 3D dental models using the comparison date. This updating/supplementing step can be used to produce an updated 3D dental model. In some implementations, the system can infer positions, shapes, and/or forms of teeth in the updated 3D dental model from the comparison data. For example, the system may be configured to produce an updated 3D dental model that restores missing anatomy in the initial 3D dental model with shape data/anatomy data/3D modeling data from prior 3D dental models. The system may be further configured to produce an updated 3D dental model that removes collisions between adjacent modeled teeth in interproximal areas of the initial 3D dental model. In some examples, the system may be configured to perform initial tooth matching using teeth relative positions, and use tooth forms/positions from prior 3D dental models to improve tooth detection in the updated 3D dental model. The system can further preform precising tooth matching using geometric tooth features from the initial 3D dental model and the prior 3D dental models. Additionally, the system can be configured to generate a gingiva model based on the prior 3D dental models, and can apply or add the gingiva model to the initial 3D dental model to produce the updated 3D dental model.

Figure 3A:
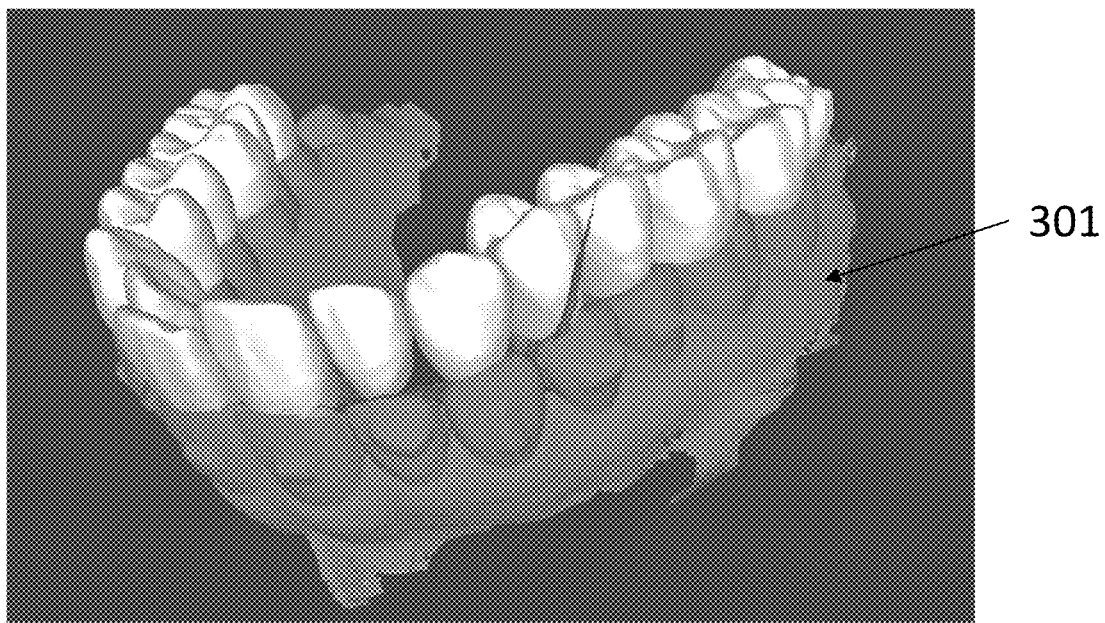

FIGS. 3A-3J illustrate one implementation of the method described in FIG. 2. FIG. 3A illustrate views of a jaw of a subject, showing an initial 3D dental model 301 (from operation 208 of FIG. 2) overlaid on a prior 3D dental model 303 (from operation 210 of FIG. 2). As shown in FIG. 3A, the system can perform a rigid transformation of teeth between the initial 3D dental model and the prior 3D dental model to match the teeth shapes as closely as possible, as is shown. The transformation can be achieved by using tooth shape similarity, teeth relative positions, and expected tooth motion trajectory from the prior 3D dental model, for example. At this stage, the initial 3D dental model can be compared to the prior 3D dental model to determine if the models are similar enough to proceed with modeling/segmentation and bypass traditional quality control processes. As described in operation 214 of FIG. 2, this threshold comparison can include comparing dental features or dentition similarity criteria of individual teeth (e.g., such as shape, position, orientation, number of teeth, number of treated jaws, tooth geometry, etc.) in the initial 3D dental model to corresponding dental features or dentition similarity criteria in the prior 3D dental model(s).

Figure 3B:
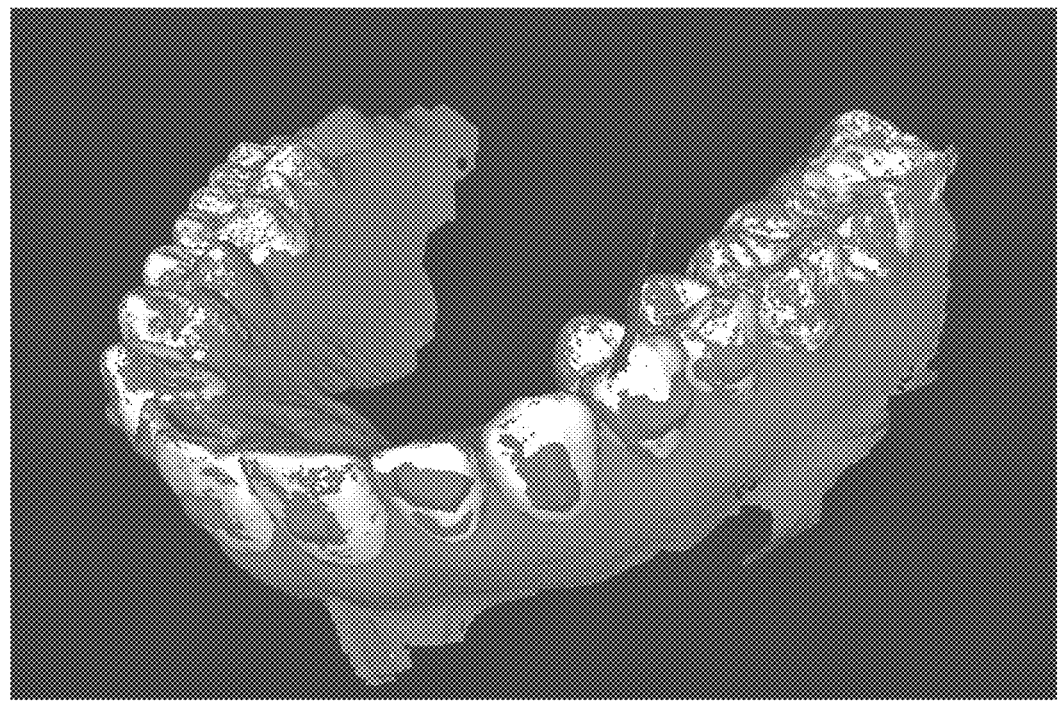

FIG. 3B is a visual representation of the initial 3D dental model overlaid on the prior 3D dental model, which can be used, as described in operation 216 of FIG. 2, to produce comparison data between the two models. The dimensions, shapes, axes, orientation, and position of the subject teeth can be calculated in both the current 3D dental model and the prior 3D dental model can be compared to produce comparison data. In this example, many parameters of the teeth in both the initial 3D dental model and the prior 3D dental model, as described above, can be measured and compared with acceptable thresholds. If any the measured parameters exceed the desired similarity thresholds, then automatic segmentation cannot be considered acceptable.

Figure 3C:
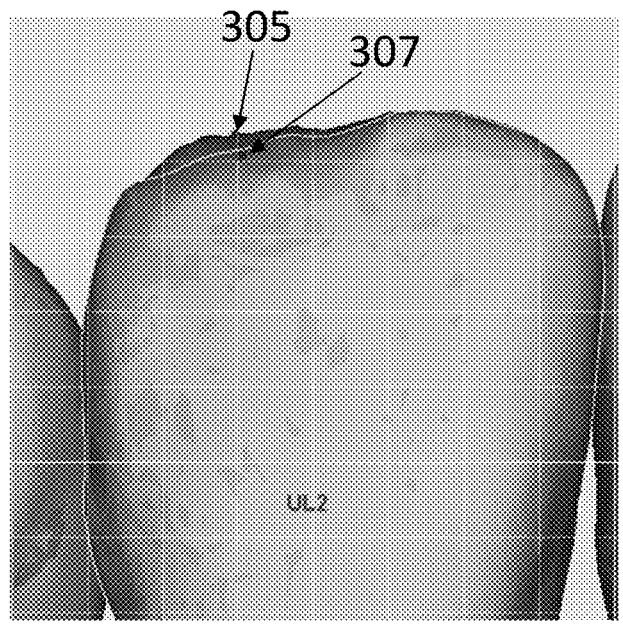
Figure 3D:
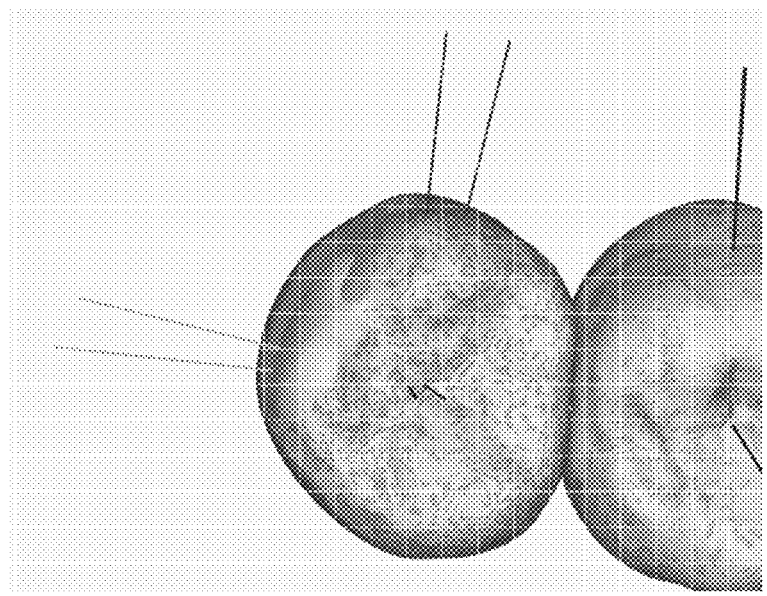

FIG. 3C is one example of a tooth shape in an initial 3D dental model that deviates beyond an acceptable similarity threshold when compared to the tooth shape of the same tooth in the prior 3D dental model. In the example of FIG. 3C, the distance between the surface 305 of a tooth in the initial 3D dental model and the surface 307 of the same tooth in the prior 3D dental model is calculated to be 0.3 mm, which is greater than the acceptable similarity threshold. In this example, since the model produced a tooth that is beyond the similarity threshold, the segmentation result in the initial 3D model may be deemed unacceptable. In case of such discrepancy, it can be difficult to determine if the deviation was caused by real anatomy changes in the subject or by scan distortions or segmentation algorithm failures. FIG. 3D is one example of precise geometric matching between the initial 3D dental model and the prior 3D dental model. In this example, geometric features such as tooth axes can be used to create tooth shape borders which can be used by the system to improve/update the initial 3D dental model.

Figure 3E:
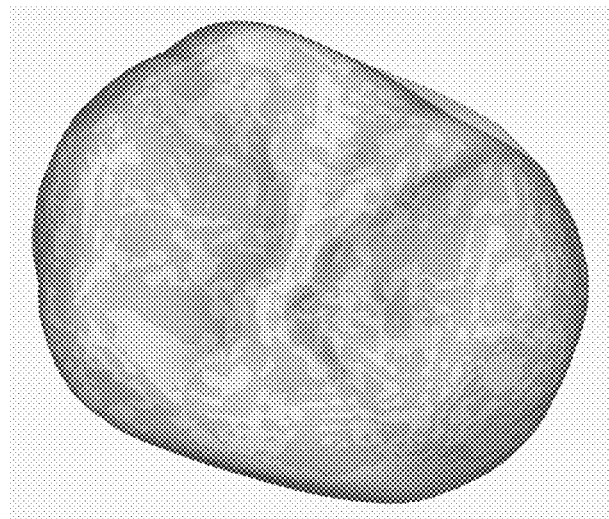
Figure 3F:
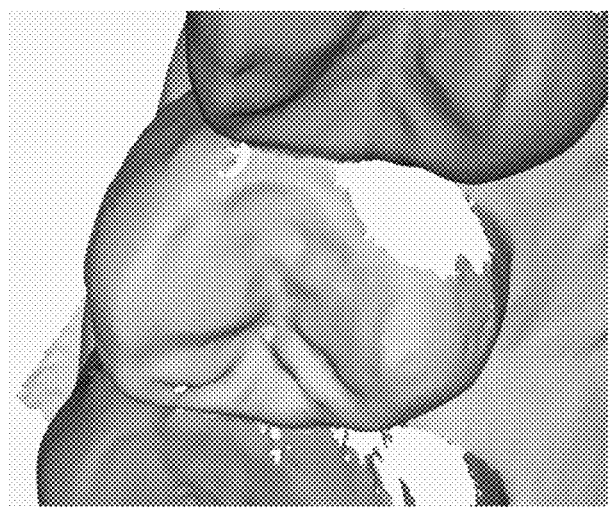

FIGS. 3E-3F illustrate two examples of errors/discrepancies/missing data in the initial 3D dental model than can be supplemented/updated with the prior 3D dental model. For example, in FIG. 3E, the prior 3D dental model for the illustrated tooth is much larger than the corresponding tooth in the initial 3D dental model. This can be caused by, for example, an error in the scan data. Similarly, in FIG. 3F, a hole in the scan surface in the area of a visible tooth crown is shown in the initial 3D dental model. In these examples, the initial 3D dental model can be updated/supplemented with the shape data from the prior 3D dental model (as described in operation 218 of FIG. 2).

As described above, the system can further be configured to use prior 3D model data to correct numeration in the initial/updated 3D dental model. FIGS. 3G and 3H illustrate an initial 3D dental model in which at least one tooth has been incorrectly numbered by the automated segmentation process. In FIG. 3G, teeth 7-10 have been mis-numbered as teeth 8-11, respectively, and in FIG. 3H, teeth 18-20 have been mis-numbered as 17-19. FIGS. 3I and 3J illustrate the updated 3D dental model with correct teeth numeration, which can be achieved by using teeth numeration data from the prior 3D dental models as described above.

Figure 4:
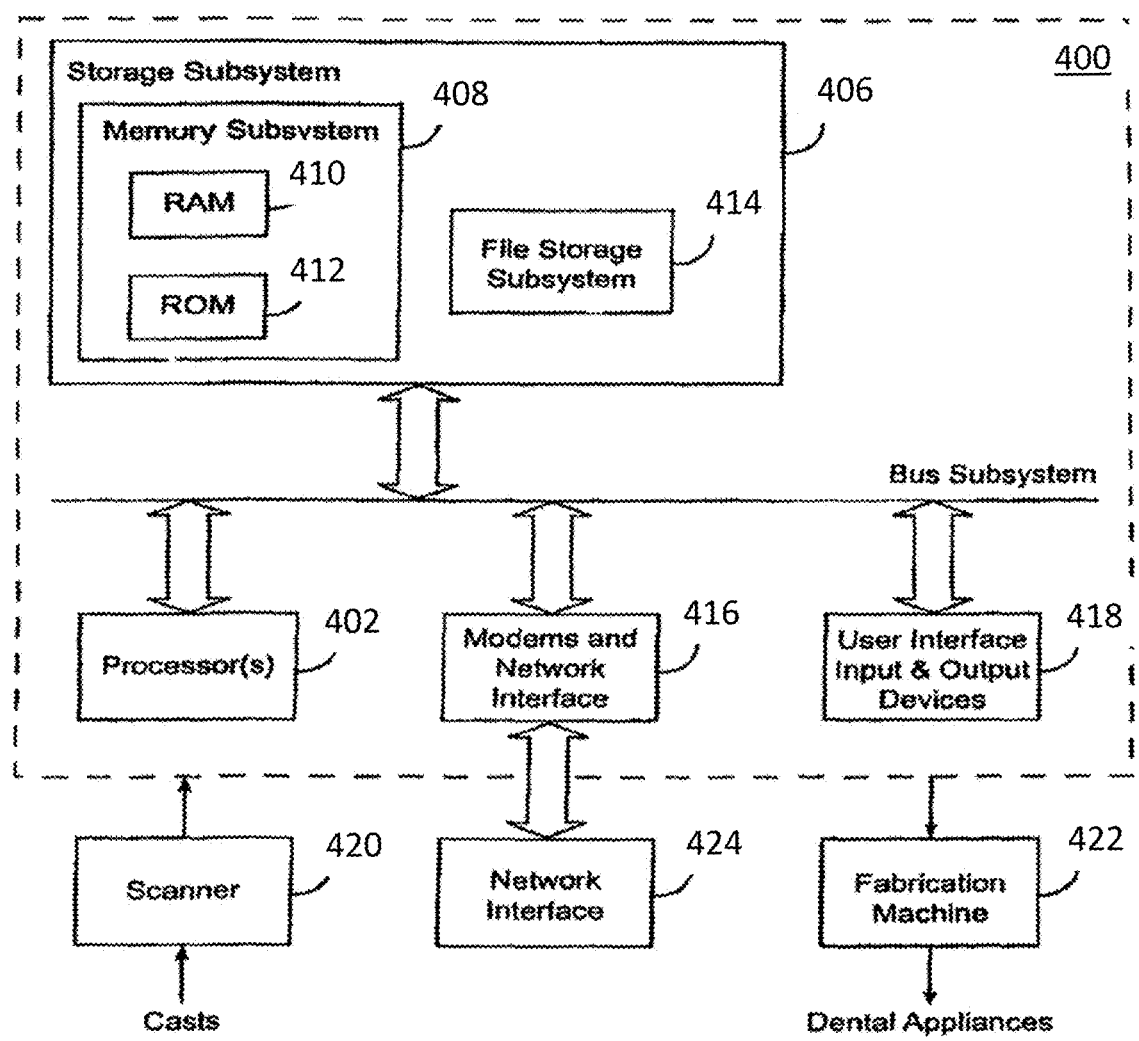
FIG. 4 is a simplified block diagram of a data processing system that may perform the methods described herein.

The methods described herein may be performed by an apparatus, such as a data processing system, which may include hardware, software, and/or firmware for performing many of these steps described above. For example, FIG. 4 is a simplified block diagram of a data processing system 400. Data processing system 400 typically includes at least one processor 402 which communicates with a number of peripheral devices over bus subsystem 404. These peripheral devices typically include a storage subsystem 406 (memory subsystem 408 and file storage subsystem 414), a set of user interface input and output devices 418, and an interface to outside networks 416, including the public switched telephone network. This interface is shown schematically as "Modems and Network Interface" block 416, and is coupled to corresponding interface devices in other data processing systems over communication network interface 424. Data processing system 400 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 406 maintains the basic programming and data constructs that provide the functionality of the present invention. The software modules discussed above are typically stored in storage subsystem 406. Storage subsystem 406 typically comprises memory subsystem 408 and file storage subsystem 414.

Memory subsystem 408 typically includes a number of memories including a main random access memory (RAM) 410 for storage of instructions and data during program execution and a read only memory (ROM) 412 in which fixed instructions are stored. In the case of Macintosh-compatible personal computers the ROM would include portions of the operating system; in the case of IBM-compatible personal computers, this would include the BIOS (basic input/output system).

File storage subsystem 414 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 404 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 420 is responsible for scanning casts of the subject's teeth obtained either from the subject or from an orthodontist and providing the scanned digital data set information to data processing system 400 for further processing. In a distributed environment, scanner 420 may be located at a remote location and communicate scanned digital data set information to data processing system 400 over network interface 424.

Fabrication machine 422 fabricates dental appliances based on intermediate and final data set information acquired from data processing system 400. In a distributed environment, fabrication machine 422 may be located at a remote location and acquire data set information from data processing system 400 over network interface 424.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

EXAMPLES

As described above, the methods and apparatuses (including non-transitory computer-readable media configured to perform any of these methods and systems incorporating such non-transitory computer-readable media) may use tooth models from previous treatments to improve orthodontic treatment planning. These improvements may in particular reduce processing time, and/or increase the speed of processing both manual and automated (including computerized) portions of treatment planning. For example, as part of an automated or semi-automated procedure, treatment planning may include generating an accurate digital model of a patient's dentition. The digital model may be generated from scans, including intraoral scans of the subject's dental arch (e.g., teeth) and/or scans (or simply 2D images, such as digital images) of a model (impression, cast, etc.) of the subject's dental arch. These digital models of the dental arch may be segmented to identify regions or sub-regions of the dental arch, teeth, gingiva, etc. The segmentation may be automated or semi-automated. In any of these processes the digital model before, during or after segmentation may be checked to verify the accuracy of the digital model and/or segmentation.

A digital model of the patient's dentition (also referred to as a digital model of the patient's dental arch, and as a digital model of the patient's teeth) may include dentition similarity criteria. Dentition similarity criteria may be features of individual teeth or groups of teeth or teeth and gingiva that may be compared between different digital representations of the subject's teeth, such as representations from earlier dental/orthodontic procedures (e.g., earlier digital models of the patient's dentition). Examples of dentition similarity criteria may include generally the shape or geometry of individual teeth or a group of teeth, or regions of teeth, tooth position (axis, position relative to adjacent teeth, rotation, etc.), tooth color, etc. Dentition similarity criteria may include metadata about the subject's teeth taken from a digital representation of the subject's dentition, such as tooth number, etc. Examples of dentition similarity criteria include: the overall number of teeth, tooth geometry in different areas, teeth numeration, number of treated jaws, FACC (facial axis of the clinical crowns), IP contacts, bite configuration, jaw axis, references representing expected tooth motion trajectory from the subject's previous dental or orthodontic treatment, etc. Dentition similarity criteria may include tooth shape similarity from the subject's previous dental or orthodontic treatment, and/or how automatic segmentation places tooth axis.

The dentition similarity criteria may provide a standardized (or a measure capable of being standardized) for rapid comparison between two digital representations of the subject's teeth. The dentition similarity criteria may refer to a single criterion or may refer to a set of similar criteria, such as a set of values corresponding to individual tooth values. For example, a dentition similarity criteria may include shapes associated with one or more of the subject's teeth.

When comparing the dentition similarity criteria, the dentition similarity criteria may be compared to each other, and the differences may be quantified and/or compared to a threshold value. For example, a comparison may provide a measure of the difference(s) between the dentition similarity criteria of different (earlier vs. current) digital models of the subject's dentition. Thus, in some examples if the differences between the dentition similarity criteria (or sets of dentition similarity criteria) are low for a particular dentition similarity criteria or set of dentition similarity criteria, such as equal to and/or less than a threshold value, then the corresponding dentition similarity criteria may be identified as correct or consistent and may be marked or otherwise indicated as correct. In some examples dentition similarity criteria that are consistent or correct when compared may be locked, to prevent further modification of these dentition similarity criterion in the updated dental model formed.

Alternatively or additionally, in some examples where the difference between dentition similarity criteria is greater than a threshold (or equal to and greater than a threshold), the earlier dentition similarity criteria, e.g., the dentition similarity criteria corresponding to the earlier treatment (a prior dental model from the subject's previous dental or orthodontic treatment) may be used as the correct dentition similarity criteria when forming an updated dental model. In this example as well, the dentition similarity criteria in the updated dental model taken from the prior treatment may be locked, to prevent further modification of these dentition similarity criterion in the updated dental model.

For example as will be described in FIGS. 5A-5B, below, the methods or apparatuses described herein may use dentition similarity criteria to confirm tooth axis. If a dentition similarity criteria such as the shapes of the teeth and axis of the teeth are similar (within threshold values) between a digital model of the subject's dentition from a prior treatment and a current digital model of the subject's dentition, then an updated digital model of the patient's dentition ("updated digital model") may be marked, such as by the use of meta information to an associated file (e.g., an IDF file) that indicated that the tooth axis placement is sufficiently accurate. This information may signal to a technician not to modify this feature (e.g., the axis) on this model. In some examples the dentition similarity criteria may be the same as the feature to be set and/or locked by the comparison, while in some examples the dentition similarity criteria may be different from, but associated with the dentition similarity criteria used for the comparison (as in the prior example, tooth shape and axis may be used to set the tooth shape). In use, the user interface may present (e.g., display) the updated dental model and may mark it visually (e.g., showing the related teeth, gingiva, or region of the tooth/gingiva) by a color or other marker (e.g., blue coloring, shading, etc.), and/or by locking the related teeth/region in the user interface to prevent the user, e.g., technician, dental professional, etc., from modifying the related teeth, gingiva and/or region. For example, the user control on the user interface may be disabled (with respect to the tool that allows the user to modify the particular feature (tooth, gingiva or region).

As described above, any of these methods and may be part of a system or method for treatment planning. For example, a method or system may receive (or in some examples may take) a digital scan of the subject's dentition. A request to form a treatment plan may be received at the same time or thereafter. The current digital scan (or collection of images) may be used to generate a digital model, which in some examples may be a three-dimensional (3D) digital model of the dentition. Dental structures, such as teeth, gingiva, etc., may then be segmented as described above. Segmentation may be performed concurrently with the scan in some examples, or may be performed after the request for a treatment plan is received. The current model may be checked as part of a digital review (DDT), which may be greatly improved by the methods and apparatuses described herein. This review process may generate an updated dental model (updated digital dental model), as described herein. The updated dental model may then be used for treatment planning and/or forming of one or more dental appliances (such as, but not limited to aligners) associated with the treatment plan. Because the dental appliance and treatment plan require a high degree of accuracy to the tooth shape and properties, these review process is critical to these procedures. The methods and apparatuses described herein may provide a significant improvement in the processing time and therefore reduction in associated costs (including in computing time).

In practice dental/orthodontic treatment may include one or more secondary orders, in which additional and/or supplemental dental appliances are required. This may occur if a subject stops and later returns to treatment, or if the treatment otherwise becomes interrupted for some reason. In such cases the patient may already have a high-quality digital model of subject's dentition as part of the most recent prior treatment, and this digital model may be used as described herein.

As part of the methods and apparatuses described herein, a database holding treatment information for patients, which may include (or may direct to) prior dental model from the subject's previous dental or orthodontic treatment. The database (patient treatment database) may include meta data or meta information that is linked to specific subjects. The database may be searched for the previous file (e.g., the prior dental model from the subject's previous dental or orthodontic treatment) for the particular subject. In some cases the database may include subjects with incomplete, interrupted or cancelled treatments for which one or more treatment plans may have been initiated, and one or more dental appliances ordered and/or used. Thus, any of these methods and apparatuses may first identify if such prior subject data exists, and if so, may access and use it as described herein (e.g., may retrieve prior dental model from the subject's previous dental or orthodontic treatment). In some cases the most recent prior dental model from the subject's previous dental or orthodontic treatment may be used. In some cases each prior dental model from the subject's previous dental or orthodontic treatment may include meta data indicating the quality of the treatment, and/or goodness of fit of the dental appliances, etc., and the prior dental model from the subject's previous dental or orthodontic treatment may be selected based on the metadata (e.g., picking the highest quality). In some cases the prior dental model from the subject's previous dental or orthodontic treatment may "time out" if too much time has passed from the prior treatment, and the prior dental model from the subject's previous dental or orthodontic treatment may be rejected and not used.

These methods an apparatuses may also be configured to detect errors or mismatches between dental models for a particular subject. In some cases there may be a mismatch; for example a doctor/orthodontist or technician may mistakenly identify a particular digital model of a subject's dentition as corresponding to an incorrect subject. For example, the method and/or apparatus may identify a mismatch where all or a majority of the dentition similarity criteria (or particular dentition similarity criteria, such as tooth shape) do not match within a reasonable threshold. Thus method or apparatus may then determine that the prior digital model does not correspond to the current patient and may flag the mismatch for the technician, and reject the prior dental model.

Prior digital models that have been used to generate one or more appliances may be used and relied on by the apparatus as the prior dental model from the subject's previous dental or orthodontic treatment for comparison to the initial segmented dental model (the current digital dental model). In general the prior dental model may already be segmented.

As part of the comparison and forming of the updated dental model, the method or apparatus may identify discrepancies in tooth modeling of the new scan (current digital dental model). For example, if the new scan has holes or gaps due to the scanning, the method or apparatus may fill these gaps or holes using data from previous digital model to form the updated dental model. The method or apparatus may also or alternatively validate the segmentation and/or improve the segmentation by using the prior dental model.

As mentioned, features that may be modified or improved in forming the updated dental model using these methods and apparatuses may include, but are not limited to: FACC, tooth numbering, tooth axes, jaw axes, painting, detailing or teeth, etc. These features may correspond to the dentition similarity criteria and/or may be related to the dentition similarity criteria used for the method or apparatus. These method and apparatuses may assume that the previous model is correct because it may be used only in cases where the subject wore the dental applied of the prior treatment plan for some time. Thus in some cases the previously undergone dental or orthodontic treatment and the corresponding dental model may be used only where a treatment plan was at least started, so that a dental appliance was worn. The database may include data (e.g., metadata) referencing an order type and/or outcome information (e.g., information about why the treatment was interrupted, discontinued, etc.) and may confirm that the dental appliance in the previously undergone dental or orthodontic treatment fit well and/or did not have associated problems (if so, the dental model from the previously undergone dental or orthodontic treatment may not be used).

Figure 5A:
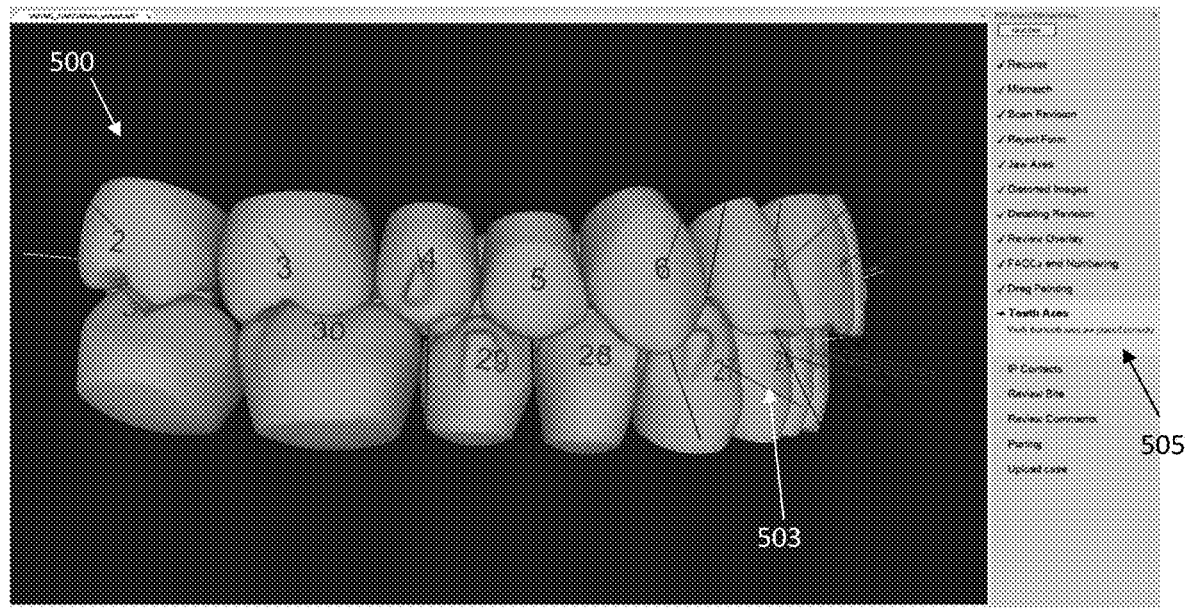
FIG. 5A illustrates an example of a user interface showing an initial segmented dental model from the dental scan.
Figure 5B:
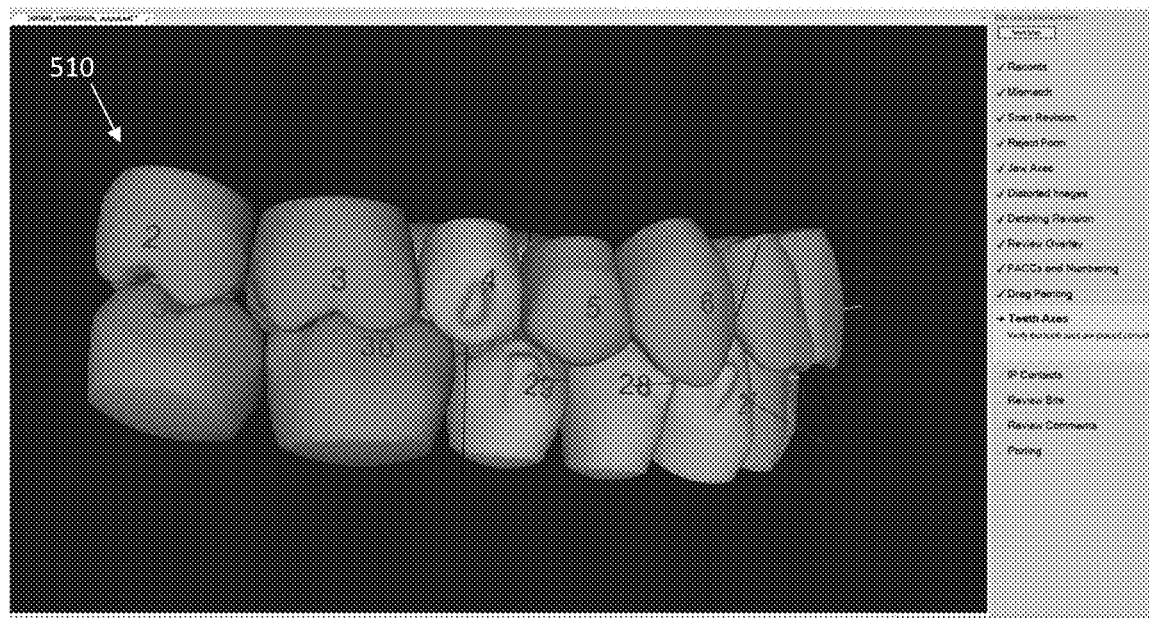
FIG. 5B shows the user interface of FIG. 5A displaying an updated dental model after performing the method described herein to verify the tooth axes.

For example, FIG. 5A shows an example of a user interface showing an initial segmented dental model from the dental scan 500, before the correction procedure described herein is performed. In this example, the teeth have been segmented and numbered (shown) and axes 503 have been indicated. The user interface may include one or more tools (e.g., controls) for checking or verifying or correcting the digital model to generate an updated dental model. For example, in FIG. 5A the user interface includes controls (buttons, toggles, menu, etc.) to verify one or more features 505; in FIG. 5A the control for verifying teeth axes is shown selected. Thereafter, the apparatus may perform the steps described above, including obtaining a prior dental model from the subject's previous dental or orthodontic treatment, e.g., by accessing a database. The apparatus may then compare dentition similarity criteria (e.g., tooth shape and/or tooth axes) between the initial segmented dental model (shown in FIG. 5A) and a prior dental model (not shown). As mentioned, the dentition similarly criteria may be the same or related to the feature(s) being verified. In FIG. 5A the apparatus is verifying tooth axes and may therefore use dentition similarly criteria related to the tooth axes. In some examples this is the tooth axes, in some examples it is the tooth axes and the tooth shape. The apparatus may then generate an update dental model by using the features being verified from the prior dental model into the initial segmented dental model when the dentition similarly criteria for each tooth or region indicates that there is a sufficient difference (greater than a threshold) with the corresponding dentition similarity criteria of the prior dental model. The updated dental model 510 is shown in FIG. 5B. In this example, teeth for which the comparison of the dentition similarity criteria is above a threshold range are shown shaded (e.g., teeth labeled 2, 3, 5, 6, 7, 31, 30, 26). These teeth may be 'locked' with respect to their axes, to prevent further modification by the user/technician. The threshold for the axis may include defined angles when the position is assumed to be the same. For example, the threshold may be, e.g., within 5 deg. In FIG. 5B the majority of the teeth may be "locked" so that the technician does not need to further modify them. The thresholds may be specific to particular teeth or types of teeth. For example, the threshold may be 2.2 degrees or less for incisors in any of x, y, z (e.g., distance of 0.4 mm or less), may be less than 3.2 degrees for canines (e.g., less than 0.6 mm), may be 4.9 degrees or less for any of x, y, z for premolars (e.g., less than 0.74 mm) and/or 6.8 degrees or less for terminal molars in x, y, z (e.g., less than 0.55 mm). In some examples, each of the axes (x, y, z) may have different corresponding thresholds).

In practice, the methods and apparatuses described herein may resulting saving of process time of approximately 30 seconds or more; since this applies to each process, this time may accumulate, resulting in savings of thousands or hours per month in higher volume processes.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the individual matter may be practiced. As mentioned, other embodiments may be utilized and derived there from, such that structural and logical substitutions and changes may be made without departing from the scope of this disclosure. Such embodiments of the inventive patient matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method for automated quality checking of a 3D model for digital treatment planning, the method comprising:
   receiving a current intraoral dental scan of a subject's dentition;
   determining if the subject has previously undergone dental or orthodontic treatment including a prior treatment plan that was completed or discontinued; and
   if the subject has previously undergone a dental or orthodontic treatment:
     generating an initial 3D segmented dental model from the current intraoral dental scan;
     obtaining a prior dental model from the subject's previous dental or orthodontic treatment;
     comparing dentition similarity criteria between the initial 3D segmented dental model and the prior dental model; and
     modifying the initial 3D segmented dental model with one or more features of the prior dental model to improve a quality of the initial 3D segmented dental model based on the comparison of the dentition similarity criteria, wherein modifying the initial 3D segmented dental model includes inferring positions and/or forms of teeth from the prior dental model, to produce an updated dental model.

2. The method of claim 1, wherein modifying the initial 3D segmented dental model comprises using the one or more features of the prior dental model when the comparison of the dentition similarity criteria is less than a threshold value.

3. The method of claim 1, wherein comparing the dentition similarity criteria comprises comparing dentition criteria that are correlated to the one or more features of the initial 3D segmented dental model.

4. The method of claim 1, wherein the one or more features of the prior dental model comprises: a tooth axis, a region of a tooth surface, a facial axis of a clinical crown, or a tooth number.

5. The method of claim 1, wherein determining if the subject has previously undergone dental or orthodontic treatment further comprises searching a historical treatment database with non-scan information.

6. The method of claim 1, wherein if the subject has not previously undergone dental or orthodontic treatment, proceeding with a traditional dental modeling and segmentation process that includes a manual quality control check by a trained professional.

7. The method of claim 1, wherein the initial 3D segmented dental model comprises a 3D dental mesh model.

8. The method of claim 1, wherein the prior dental model is a final 3D model from the subject's previous dental or orthodontic treatment.

9. The method of claim 1, wherein the dentition similarity criteria are based on multiple treatment plan parameters that were applied during the subject's previous dental or orthodontic treatment.

10. The method of claim 1, wherein the dentition similarity criteria are one or more of an overall number of teeth, a tooth geometry in different areas, teeth numeration, or a number of treated jaws.

11. The method of claim 1, wherein the dentition similarity criteria are references representing tooth shape similarity from the subject's previous dental or orthodontic treatment.

12. The method of claim 1, wherein the dentition similarity criteria are references representing expected tooth motion trajectory from the subject's previous dental or orthodontic treatment.

13. The method of claim 1, wherein comparing the dentition similarity criteria further comprises calculating a rigid transformation of teeth in the initial 3D segmented dental model having references matching shapes to corresponding teeth in the prior dental model.

14. The method of claim 1, wherein modifying the initial 3D segmented dental model further comprises restoring missing anatomy with shape data from the prior dental model.

15. The method of claim 1, wherein modifying the initial 3D segmented dental model further comprises updating teeth axes with axes data from the prior dental model.

16. The method of claim 1, wherein modifying the initial 3D segmented dental model further comprises performing initial tooth matching using teeth relative positions between the initial 3D segmented dental model and the prior dental model.

17. The method of claim 1, wherein modifying the initial 3D segmented dental model further comprises performing precise tooth matching using geometric tooth features between the initial 3D segmented dental model and the prior dental model.

18. The method of claim 1, wherein modifying the initial 3D segmented dental model further comprises removing interproximal area collisions in the initial 3D segmented dental model based on the prior dental model.

19. The method of claim 1, wherein modifying the initial 3D segmented dental model further comprises correcting tooth shapes and gingival lines using borders based on the prior dental model.

20. The method of claim 1, wherein modifying the initial 3D segmented dental model further comprises enumerating the initial 3D segmented dental model with a numeration of the prior dental model.

21. The method of claim 1, further comprising automatically trimming the updated dental model based on a trim line of the prior dental model.

22. A non-transitory computer-readable medium including contents that are configured to cause one or more processors to perform a method for automated quality checking of a 3D model for digital treatment planning, comprising:
receiving a current intraoral dental scan of a subject's dentition;
determining if the subject has previously undergone dental or orthodontic treatment including a prior treatment plan that was completed or discontinued; and
if the subject has previously undergone dental or orthodontic treatment:
generating an initial 3D segmented dental model from the current intraoral dental scan;
obtaining a prior segmented dental model from the subject's previous dental or orthodontic treatment;
comparing dentition similarity criteria between the initial 3D segmented dental model and the prior segmented dental model; and
modifying the initial 3D segmented dental model with one or more features of the prior segmented dental model to improve a quality of the initial 3D segmented dental model based on the comparison of the dentition similarity criteria, wherein modifying the initial 3D segmented dental model includes inferring positions and/or forms of teeth from the prior segmented dental model, to produce an updated dental model.

23. A non-transitory computer-readable medium including contents that are configured to cause one or more processors to perform a method for automated quality checking of a 3D model for digital treatment planning, comprising:
generating an initial 3D segmented dental model from a current intraoral dental scan of a subject's dentition;
comparing dentition similarity criteria between the initial 3D segmented dental model from the current intraoral dental scan and a prior dental model including a prior treatment plan that was completed or discontinued; and
modifying the initial 3D segmented dental model from the current intraoral dental scan with one or more features from the prior dental model to improve a quality of the initial 3D segmented dental model based on the comparison of the dentition similarity criteria, wherein modifying the initial 3D segmented dental model includes inferring positions and/or forms of teeth from the prior dental model, to produce an updated dental model;
displaying the updated dental model in which the one or more features from the prior dental model are marked; and
permitting a user to modify the updated dental model from the display, but preventing the user from modifying the marked one or more features.

* * * * *